(12) United States Patent
Overbeck et al.

(10) Patent No.: US 7,050,168 B2
(45) Date of Patent: May 23, 2006

(54) OPTICAL MEASUREMENT DEVICE AND RELATED PROCESS

(75) Inventors: James L. Overbeck, Ada, MI (US); Richard J. Van Andel, Grand Rapids, MI (US)

(73) Assignee: X-Rite, Incorporated, Grandville, MI (US)

( * ) Notice: Subject to any disclaimer, the term of this patent is extended or adjusted under 35 U.S.C. 154(b) by 415 days.

(21) Appl. No.: 09/733,162

(22) Filed: Dec. 8, 2000

(65) Prior Publication Data

US 2003/0189706 A1   Oct. 9, 2003

Related U.S. Application Data

(60) Provisional application No. 60/169,638, filed on Dec. 8, 1999.

(51) Int. Cl.
*G01N 21/25* (2006.01)

(52) U.S. Cl. .......................... 356/407; 356/408; 433/29

(58) Field of Classification Search ................ 356/405, 356/406, 407, 416, 419, 73, 243.1, 408; 433/26, 433/29, 203.1; 607/198
See application file for complete search history.

(56) References Cited

U.S. PATENT DOCUMENTS

| | | |
|---|---|---|
| 3,436,157 A | 4/1969 | Adler |
| 3,778,541 A | 12/1973 | Bowker |
| 3,802,783 A | 4/1974 | Simmonds et al. |
| 3,929,398 A | 12/1975 | Bates |
| 3,986,777 A | 10/1976 | Roll |
| 4,096,217 A | 6/1978 | Roll |
| 4,125,329 A | 11/1978 | French et al. |
| 4,131,367 A | 12/1978 | French et al. |
| 4,241,738 A | 12/1980 | Lübers et al. |

(Continued)

FOREIGN PATENT DOCUMENTS

AU   261091   9/1961

(Continued)

OTHER PUBLICATIONS

*General Characteristics of an LSD®*, (visited Oct. 26, 2000) <http://www.poc.com/hgram/techdata/general.htm> Printout.

(Continued)

*Primary Examiner*—Layla G. Lauchman
(74) *Attorney, Agent, or Firm*—Kirkpatrick & Lockhart Nicholson Graham LLP

(57) ABSTRACT

An instrument and related process for measuring color, shade, gloss, shape and/or translucence of a tooth. First, the instrument uses searchlight illumination to illuminate a tooth with constant irradiance. Second, the instrument uses calorimetric imaging to collect time-separated frames of different wavelengths of light reflected from a tooth and to combine those frames into a color image. Third, the instrument includes a sanitary shield to establish a reference color and a predetermined distance to a target tooth. Fourth, the instrument provides line-of-sight viewing so an operator may simultaneously view a display of the image on the instrument and the object being measured. Fifth, the instrument is impervious to pollutants because it incorporates a sealed measurement window. Sixth, optical measurements of a tooth taken by a dentist are compared to optical measurements of a prosthetic restoration for that tooth to confirm satisfactory matching of optical characteristics of the tooth and restoration.

18 Claims, 16 Drawing Sheets

U.S. PATENT DOCUMENTS

| | | |
|---|---|---|
| 4,247,202 A | 1/1981 | Failes |
| 4,414,635 A | 11/1983 | Gast et al. |
| 4,518,258 A | 5/1985 | Broersma |
| 4,547,074 A | 10/1985 | Hinoda et al. |
| 4,575,805 A | 3/1986 | Moermann et al. |
| 4,611,288 A | 9/1986 | Duret et al. |
| 4,623,973 A | 11/1986 | Hoffrichter et al. |
| 4,654,794 A | 3/1987 | O'Brien |
| 4,678,338 A | 7/1987 | Kitta et al. |
| 4,692,481 A | 9/1987 | Kelly |
| 4,773,097 A | 9/1988 | Suzaki et al. |
| 4,812,904 A | 3/1989 | Maring et al. |
| 4,818,231 A | 4/1989 | Steiner et al. |
| 4,836,674 A | 6/1989 | Lequime et al. |
| 4,837,732 A | 6/1989 | Brandestini et al. |
| 4,881,811 A | 11/1989 | O'Brien |
| 4,964,692 A | 10/1990 | Prescott |
| 5,003,500 A | 3/1991 | Gerber |
| 5,012,431 A | 4/1991 | Stanziola |
| 5,017,140 A | 5/1991 | Ascher |
| 5,051,823 A | 9/1991 | Cooper et al. |
| 5,124,797 A | 6/1992 | Williams et al. |
| 5,150,199 A | 9/1992 | Shoemaker et al. |
| 5,155,558 A | 10/1992 | Tannenbaum et al. |
| 5,177,694 A | 1/1993 | Graham et al. |
| 5,231,472 A | 7/1993 | Marcus et al. |
| 5,240,414 A | 8/1993 | Thompson |
| 5,241,170 A | 8/1993 | Field, Jr. et al. |
| 5,278,674 A | 1/1994 | Webb et al. |
| 5,313,267 A | 5/1994 | MacFarlane et al. |
| 5,319,437 A | 6/1994 | Van Aken et al. |
| 5,373,364 A | 12/1994 | Krzyminski |
| 5,383,020 A | 1/1995 | Vieillefosse |
| 5,408,992 A | 4/1995 | Hamlin et al. |
| 5,428,450 A | 6/1995 | Vieillefosse et al. |
| 5,477,332 A | 12/1995 | Stone et al. |
| 5,483,339 A | 1/1996 | Van Aken et al. |
| 5,484,283 A | 1/1996 | Franetzki |
| 5,493,404 A | 2/1996 | Allaire et al. |
| 5,526,285 A | 6/1996 | Campo et al. |
| 5,530,632 A | 6/1996 | Shikano |
| 5,599,278 A | 2/1997 | Hibbard |
| 5,636,040 A | 6/1997 | Tung |
| 5,654,809 A | 8/1997 | Beeman et al. |
| 5,658,235 A | 8/1997 | Priest et al. |
| 5,661,519 A | 8/1997 | Franetzki |
| 5,690,486 A | 11/1997 | Zigelbaum |
| 5,690,605 A | 11/1997 | Hamlin et al. |
| 5,745,229 A | 4/1998 | Jung et al. |
| 5,759,030 A | 6/1998 | Jung et al. |
| 5,766,006 A | 6/1998 | Murljacic |
| 5,798,839 A | 8/1998 | Berner et al. |
| 5,822,052 A | 10/1998 | Tsai |
| 5,836,762 A | 11/1998 | Peithman |
| 5,850,472 A | 12/1998 | Alston et al. |
| 5,851,113 A | 12/1998 | Jung et al. |
| 5,851,115 A | 12/1998 | Carlsson et al. |
| 5,871,351 A | 2/1999 | Jung et al. |
| 5,880,826 A | 3/1999 | Jung et al. |
| 5,883,708 A | 3/1999 | Jung et al. |
| 5,893,712 A | 4/1999 | Stone et al. |
| 5,902,246 A | 5/1999 | McHenry et al. |
| 5,924,981 A | 7/1999 | Rothfritz et al. |
| 5,961,324 A | 10/1999 | Lehmann |
| 5,967,775 A | 10/1999 | Shahid et al. |
| 5,995,243 A | 11/1999 | Kerschner et al. |
| RE36,434 E | 12/1999 | Hamlin et al. |
| 6,007,332 A | 12/1999 | O'Brien |
| 6,008,905 A | 12/1999 | Breton et al. |
| 6,019,721 A | 2/2000 | Holmes et al. |
| 6,030,209 A | 2/2000 | Panzera et al. |
| 6,031,233 A | 2/2000 | Levin et al. |
| 6,038,024 A | 3/2000 | Berner |
| 6,040,902 A | 3/2000 | Jung et al. |
| 6,075,949 A | 6/2000 | Hatakenaka et al. |
| 6,093,019 A | 7/2000 | Morandi et al. |
| 6,095,811 A | 8/2000 | Stearns |
| 6,102,696 A | 8/2000 | Osterwalder et al. |
| 6,106,457 A | 8/2000 | Perkins et al. |
| 6,111,650 A | 8/2000 | Rawicz et al. |
| 6,118,521 A | 9/2000 | Jung |
| 6,132,210 A | 10/2000 | Lehmann |
| 6,185,851 B1 | 2/2001 | Loudermilk et al. |
| 6,188,471 B1 | 2/2001 | Jung et al. |
| 6,205,258 B1 | 3/2001 | Lin |
| 6,206,691 B1 | 3/2001 | Lehmann et al. |
| 6,210,159 B1 | 4/2001 | Lehmann et al. |
| 6,222,620 B1 | 4/2001 | Jung et al. |
| 6,231,343 B1 | 5/2001 | Ishibashi et al. |
| 6,233,047 B1 | 5/2001 | Jung et al. |
| 6,239,868 B1 | 5/2001 | Jung et al. |
| 6,246,479 B1 | 6/2001 | Jung et al. |
| 6,249,340 B1 | 6/2001 | Jung et al. |
| 6,249,348 B1 | 6/2001 | Jung et al. |
| 6,254,385 B1 | 7/2001 | Jung et al. |
| 6,271,913 B1 | 8/2001 | Jung et al. |
| 6,297,882 B1 | 10/2001 | Moisio |
| 6,301,004 B1 | 10/2001 | Jung et al. |
| 6,307,629 B1 | 10/2001 | Jung et al. |
| 6,328,563 B1 | 12/2001 | Hobo |
| 6,331,113 B1 | 12/2001 | Morris et al. |
| 6,381,017 B1 | 4/2002 | Jung et al. |
| 6,432,046 B1 | 8/2002 | Yarush et al. |
| 6,445,812 B1 | 9/2002 | Lai et al. |
| 6,570,654 B1 | 5/2003 | Jung et al. |
| 2001/0023056 A1 | 9/2001 | Grunenfelder et al. |
| 2001/0023058 A1 | 9/2001 | Jung et al. |
| 2001/0029009 A1 | 10/2001 | Jung et al. |
| 2001/0038451 A1 | 11/2001 | Jung et al. |
| 2001/0038453 A1 | 11/2001 | Jung et al. |
| 2001/0049083 A1 | 12/2001 | Jung et al. |
| 2002/0003620 A1 | 1/2002 | Jung et al. |
| 2002/0018209 A1 | 2/2002 | Jung et al. |
| 2002/0024653 A1 | 2/2002 | Jung et al. |
| 2002/0085248 A1 | 7/2002 | Xu et al. |
| 2002/0100863 A1 | 8/2002 | Spears |

FOREIGN PATENT DOCUMENTS

| | | |
|---|---|---|
| DE | 2256355 | 6/1972 |
| DE | 19534517 | 3/1997 |
| EP | 0360657 | 3/1990 |
| EP | 367647 | 5/1990 |
| EP | 0775299 B1 | 5/1997 |
| EP | 837659 | 4/1998 |
| EP | 928957 | 7/1999 |
| EP | 0739191 | 1/2002 |
| FR | 2669526 | 5/1992 |
| GB | 771805 | 11/1953 |
| JP | 4301530 | 10/1992 |
| JP | 4338465 | 11/1992 |
| JP | 9210792 | 8/1997 |
| WO | WO8603292 | 6/1986 |
| WO | WO9112955 | 3/1991 |
| WO | WO9701308 | 1/1997 |
| WO | WO9721114 | 6/1997 |
| WO | WO9725913 | 7/1997 |
| WO | WO9735513 | 10/1997 |
| WO | WO9741767 | 11/1997 |
| WO | WO9802107 | 1/1998 |
| WO | WO9812985 | 4/1998 |
| WO | WO9901745 | 1/1999 |

| | | |
|---|---|---|
| WO | WO9931472 | 6/1999 |
| WO | WO9956658 | 11/1999 |
| WO | WO0012026 | 3/2000 |
| WO | WO0025696 | 5/2000 |
| WO | WO0026847 | 5/2000 |
| WO | WO0063661 | 10/2000 |
| WO | WO0132097 | 5/2001 |
| WO | WO0135855 | 5/2001 |

OTHER PUBLICATIONS

J.D. Scheuch, *Modeling of constant irradiance illumination system*, SPIE Journal, vol. 3428, at 22-27 (1998).

International Searching Authority, Partial International Search in PCT Application PCT/US00/33478 issued on May 8, 2001.

US 6,100,988, 08/2000, Jung et al. (withdrawn)

OPTICAL MEASUREMENT DEVICE AND RELATED PROCESS

BACKGROUND OF THE INVENTION

This application claims the benefit of U.S. Provisional Application No. 60/169,638, filed Dec. 8, 1999 and entitled DENTAL VISION SYSTEM.

The present invention relates to instruments for measuring optical characteristics—for example color, translucency, and/or gloss—of objects and, more particularly, to such instruments for use in dental applications.

The determination of shade or color of an object is a process that is frequently performed in the field of dentistry. To perform dental restorations of a damaged tooth, a dentist visually compares the color of the tooth to be replaced with an assortment of shade tabs. These shade tabs are physical tabs representing the color of commercially available restorative material, such as ceramics. The tabs include the exact specification of materials needed to produce a restorative tooth with the shade of the original tooth as determined by the dentist's visual comparison. Once the dentist finds a shade tab that matches the color of the tooth, or remaining adjacent teeth in some cases, he is in a position to manufacture the required restoration. This process, however, is very time consuming and quite subjective, and frequently results in poorly shaded restorations.

In the field of dentistry, intraoral cameras are frequently used to acquire images of teeth and determine treatment plans for cavities and other mechanical reconstruction. These cameras are designed to be versatile and able to collect measurements in tight places often found in the mouth; however, they do not preserve the color fidelity—that is, they do not collect the true color—of the object measured.

Some dentists attempt to use intraoral cameras to assist in the shade determination process. Unfortunately, conventional intraoral cameras suffer two problems: distance sensitivity due to illumination geometry and color discrimination error due to sensor limitations.

With regard to the first problem, intraoral cameras typically use fiberoptic illumination to reduce the size of the handpiece. Such a device is disclosed in U.S. Re. Pat. No. 36,434 to Hamlin et al, reissued Dec. 7, 1999. The goal of Hamlin, and most intraoral cameras, is to provide a small measuring tip on a handpiece that can be used to probe hard to reach areas in a mouth. Although fiber-optic illumination is useful for providing high levels of illumination and is compatible with small measuring probe tips, a drawback of any small illumination source that illuminates a larger area is that the projected beam must be divergent light. The intensity of a divergent beam is governed by the inverse square law given below:

$$I = \frac{D^2}{(D + \Delta D)^2} \quad (1)$$

where I is intensity, D is the distance from the illumination source, and $\Delta D$ is an increase in distance D from the light source. The concept of Equation 1 is illustrated in FIG. 1, where fiber optic source 115 projects illumination flux 112 to distances D and D plus $\Delta D$. There, the intensity of flux 112 at distance D, according to Equation 1, is greater at distance D from light source 115 than at a distance D plus $\Delta D$.

It is known that when the distance change to the illumination source is significant with respect to the distance to the source, the illumination output varies significantly, creating what is called non-uniform illumination. Particularly with objects positioned close to the fiber optics, certain regions of the object are non-uniformly illuminated because the light from the illumination source rapidly diffuses as it travels away from the source. Moreover, when multiple sources of light are used to illuminate an object, the object may be non-uniformly illuminated in different regions.

An example of non-uniform illumination of the surface of an object is understood with further reference to FIG. 1. As depicted there, a curved surface of a tooth T, slightly exaggerated for purposes of discussion, is illuminated within flux 112 projected from light source 115. Region of the tooth 113, lies distance D from light source 115, and region 114, lies distance D plus $\Delta D$ from the light source 115. As explained above, the intensity of light is greater at distance D than at D plus $\Delta D$. Accordingly, regions 113 and 114 are not illuminated with the same intensity of light, that is, illumination is non-uniform. Sensors sensing light reflected from tooth T will collect inconsistent color information from these regions.

An example of non-uniform illumination of regions of an object with a multiple fiber optic light sources is illustrated in FIG. 2. Exemplary fiber optic light sources 120 and 122 project light fluxes 130 and 140 to illuminate the tooth T. These light fluxes reflect from the tooth and are collected by an image sensor not shown for the sake of simplicity. As can be seen, tooth region 122 is illuminated primarily by light flux 140, but region 124 is illuminated by a combination of light fluxes 130 and 140. Of course, this illumination is three-dimensional even though it is depicted here in only two dimensions. Further, if more fiber optic light sources are added, the tooth is subdivided into even more regions of different illumination overlap. Given this non-uniform illumination, a color sensor, sensing the light reflected from the tooth, will invariably collect inconsistent color information from region to region. For example, what is sensed as "lighter shade" in region 122 may be sensed as "darker shade" in region 124 due to the non-uniform illumination.

With non-uniform illumination, conventional intraoral cameras critically rely on illumination source positioning which can not be maintained in practical use. This results in significant errors affecting tooth shade determination.

Other devices, specifically designed for tooth shade determination, have been proposed that use bi-directional fiber optic illumination. Such a method is described in U.S. Pat. No. 6,038,024 to Berner, issued Mar. 14, 2000. A limitation of this method of illumination is that the illuminant intensity is maximized at the intersection of the two projected beams. Often, significant portions of the measured area are not illuminated by both beams and hence have a lower and unpredictable illumination value.

Berner's non-uniform illumination is depicted in FIG. 3. A fiber optic bundle 150 is supplied with light at one end. Prior to arriving at the probe tip, the bundle is bifurcated, or divided into two bundles 152 and 154. The bundles are mechanically aimed at the target tooth T in some fixed angularity. Collimating lenses 156, 158 are often added in the path of illumination between the fiber optic bundle and the target T to lower distance sensitivity of illumination output. Each bundle generates a light flux 162 and 164 projected onto tooth T from two directions with collimating lenses 156, 158. As can be seen, fluxes 162 and 164 intersect on tooth T resulting in the intensity in region 169 being greater than the intensities in regions 167 and 171 because those regions 167 and 171, and other peripheral regions, are each illuminated by light fluxes 164 and 162 individually. The fluxes reflected from the tooth T are not shown for simplicity.

Given this non-uniform illumination, a color sensor, sensing the light reflected from the tooth, will invariably collect inconsistent color value information from region to region. For example, what is sensed as "lighter shade" in region 167 may be sensed as "darker shade," in region 169 due to the non-uniform illumination. Moreover, with multiple light source paths, gloss artifact potential is increased. Where glare artifacts exist, the color of the target is washed out by the image of the light source itself rather than the desired tooth subject.

In addition to non-uniform illumination, today's intraoral cameras utilize color filter array (CFA) image sensors that frequently contribute to inaccurate color measurement because the filter array is applied to the image. Many intraoral cameras include color filter arrays such as red, green and blue (RGB) arrays, and cyan, magenta, yellow and green (CMYG) arrays, to name a few. Generally, these color filter arrays are made up of a multitude of adjacent elements called "pixels" (i.e., picture elements). Each pixel measures only the bandwidth of light it is designed to collect. Therefore, in a region of a image corresponding to a pixel, only the bandwidth of light specific to that pixel is displayed, even though the object measured may include other colors in that region.

The operation of and problems associated with color filter arrays are more readily understood with reference to a particular array. A few pixels of a CFA RGB sensor are illustrated in FIG. 4 as R, B, G. These R, G, and B pixels collect, capture or sense light corresponding to red, green and blue wavelengths impinging on the sensor respectively. The RGB sensor converts these collected wavelengths into electronic data and passes this data to a processor for display of a color image of the tooth on a monitor. Although RGB sensors offer a means to collect color data for a tooth, that data often is not an accurate representation of the true color or distribution of color on the tooth.

CFAs do not accurately measure color primarily because of two factors: pixel spacing separation and poor color fidelity. First, the pixel spacing separation factor may be understood with reference to the RGB sensor in FIG. 4. Each individual R, G, and B pixel in the RGB array 100 collects only one bandwidth of light reflected from a point on a tooth, for example, only red, only green, or only blue. Thus, when tooth sections 101 and 102 are illuminated and reflect light toward the RGB array and that light is detected by the corresponding G and B pixels respectively, only green bandwidths are collected by the green pixel and only blue bandwidths are collected by the B pixel. Even though section 101 actually may be blue, green, red, yellow or any other color of the spectrum, and consequently reflect the associated bandwidths, only the green bandwidth, if any, is detected by pixel G in section 101. Similarly, section 102 may be green or any other color, but those colors are not detected by the B pixel because blue is the only bandwidth that it can collect.

Accordingly, RGB sensors collect only one bandwidth for each point on the tooth even though that point may reflect many bandwidths. As a result, any measurement data for that point will include only data selectively collected by the R,G, or B pixel associated with that point. Moreover, prosthesis manufactured from this measurement data collected with an RGB sensor will not accurately reflect the true color of each point on the tooth. This phenomenon applies to all CFA sensors.

The second factor affecting color measurement is poor color fidelity of CFAs. The mass market for color sensors, in particular CFAs, is consumer electronics and video applications. The goal of such devices is to provide good image resolution, high image acquisition speed and reasonable color fidelity as needed for broadcast and personal imaging applications. CFAs are designed to be inexpensive to manufacture, to provide direct acquisition of RGB data and to provide reasonable low light performance. These design goals come at the cost of color fidelity. More specifically, today's RGB CFA collects selected wavelengths of light impinging on them, but they also incidentally collect unwanted wavelengths in the process. For example, a blue pixel of an RGB array is coated with a polymer that is designed to (a) allow only light of blue bandwidths to be transmitted through the polymer—acting like a filter—and sensed by that pixel, and (b) attenuate all other wavelengths, that is, prevent them from being sensed by that pixel. Typical CFA filters attenuate unwanted wavelengths by only $\frac{1}{10}^{th}$ of the value of the maximum transmittance of the filter. This lack of rejection of light outside of the wavelengths of interest degrades color fidelity to an unacceptable level for accurate color measurement.

Due to signal detection problems caused by pixel spacing and poor color fidelity, CFA-type sensors are not accurate enough for satisfactory determination of tooth shade.

Currently, most intraoral cameras include a sheath to cover the illuminating portion and/or image sensor. Conventional sheaths are disposable, so that they may be replaced if they accidentally or intentionally come in contact with a patient's mouth. By replacing a sheath between measurements on different patients, a dentist may prevent spread of contaminants, such as infectious agents, from a first patient to subsequent patient. Although these protective sheaths prevent spread of contaminants, their functionality is limited exclusively to this sanitary purpose.

Conventional intraoral cameras also include a handheld probe that a dentist inserts into a patient's mouth and collects color images with. Via a cable, the probe transmits collected color measurement to a computer that subsequently processes the measurements to create images and displays those images on a monitor for the dentist to view. The drawback in collecting images of a tooth with these conventional probes is that the dentist must look back and forth from the probe to the monitor to insure the probe is positioned over the tooth to obtain the desired image on the monitor. This, of course can cause unneeded frustration in aligning the probe to collect measurements of the tooth.

In many instances, intraoral cameras or parts thereof intentionally or accidentally come into contact with a patient's intraoral cavity thereby transmitting contaminants including infectious agents, saliva and/or food debris to the device. In addition to using sanitary sheaths as discussed above, operators of prior art intraoral cameras frequently clean or sterilize the cameras. This is often a tedious task, as the cameras include a plurality of buttons that are difficult to clean around and/or fiber optic bundles that are nearly impossible to sterilize without damaging the optical characteristics of the fibers because sterilization agents enter the fiber optics and degrade illumination or sensing capabilities. Accordingly, prior art camera users must exercise time-consuming care in operating and cleaning these cameras.

Typically, a dentist makes a shade determination visually using shade tabs. A prescription describing the restoration location and shade is sent to the dental laboratory. There, a technician attempts to duplicate the tooth shade to make prosthesis from available ceramic or synthetic materials. Once the prosthesis is manufactured, it is sent back to the dentist for installation in the patient.

Only after placing the prosthesis in proximity to the patient's damaged tooth and/or surrounding teeth can the dentist determine if the prosthesis is an acceptable duplicate of the damaged tooth. Of course, if the prosthesis does not match properly, the dentist must have a second prosthesis made by a lab incorporating his suggested modifications. A second shade determination of the tooth may even be required. The second prosthesis must also be compared by the dentist to the damaged tooth to insure a proper match. This process is very costly if multiple prosthetic replacements must be produced to create a satisfactory match. Moreover, this process consumes the time of patients who may come in for repeated visits before a matching prosthesis is created.

SUMMARY OF THE INVENTION

The aforementioned problems are overcome by the present invention wherein an optical measurement instrument uses searchlight illumination and calorimetric imaging to collect optical characteristic measurements of objects such as teeth.

The present invention uses searchlight illumination to uniformly illuminate an object when measuring the optical characteristics, such as color, shade, translucence, shape and/or gloss of that object. "Searchlight illumination" refers to illumination wherein all points of the object measured are illuminated with constant irradiance. Searchlight illumination is readily understood with reference to FIG. 5. An illuminator 80 includes light source 520 and lens 528, which is preferably an achromatic doublet lens. Any type of uniform and diffuse light source may be substituted for the illuminating integrating sphere 518. The preferred source provides a spectrum of light that is continuous in radiant power across the visible wavelength range. Light of this type may be generated from an incandescent source filtered through heat absorbing glass. The lens 528 is set to a distance of the focal length of the lens from the light source 520 so that the lens projects light rays 530 and 540 on the tooth T. Accordingly, the entire region 522, that is the entire side of the tooth being measured is uniformly illuminated with the constant irradiance of rays 530*a* and 540*a*.

Searchlight illumination offers significant benefits in the optical measurement context. First, image sensors used with searchlight illumination consistently collect optical information from light reflected from an object because the illumination is uniform over the object. Second, searchlight illumination does not vary significantly when the distance between the object and the instrument is increased as with conventional intraoral camera illumination systems. Accordingly, the positioning of the illumination source from the tooth may be varied without significantly sacrificing consistent optical information sensing. Third, with searchlight illumination, the occurrence of glare artifacts is diminished; and the optical characteristics of the object measured by a sensor are not washed out by this glare.

In another aspect of the invention, the preferred optical measurement instrument implements colorimetric imaging to measure the optical characteristics of objects. Colorimetric imaging is a process wherein multiple time-separated measurements, or "frames," of specific ranges of bandwidths of light in the visible spectrum are collected for all points on an object measured with an image sensor, preferably a monochrome image sensor. These frames are then combined to form a color image of the measured object, incorporating each collected frame and consequently each collected bandwidth. When combined, every point on each frame is aligned with its corresponding points on each other frame. When all the frames are combined, the resultant image depicts every point on the tooth and every bandwidth collected for that point on the tooth.

In the preferred embodiment, light reflected from an object, also referred to herein as "radiant flux," is sequentially transmitted through multiple filters that selectively absorb some wavelengths and transmit others to a monochromatic image sensor. These filters preferably have well controlled bandpass functions, that is, the filters allow specifically desired wavelengths of light to be transmitted to the sensor. These filters are specified by spectral transmittance curves. Preferably, the filters significantly attenuate wavelengths outside of the specified band pass function. Accordingly, these filters have very high color fidelity. Of course, depending on the application, the attenuation and transmission of certain wavelengths may be varied as desired.

In the preferred embodiment, each of these filters transmits a preferred range of bandwidths corresponding to Commission Internationale dei'Eclairage ("CIE") tristimulus value bandwidths, for example, X, Y, Z and X' tristimulus bandwidths. Tristimulus values relate to the spectral sensitivity of the human eye. Instruments that measure using these bandwidth shapes correlate highly with data generated from human color perception. In this manner, the monochromatic image sensor collects only one bandwidth or range of bandwidths at time. These individual, collected bandwidths are recorded as frames by the image sensor, converted to electric signals and transferred to a processor. The processor combines and aligns these frames to form an image including all the collected bandwidths for every point on the image.

The problems inherent in the RGB sensors of prior art intraoral cameras, specifically pixel spacing separation and poor color fidelity, are eliminated with colorimetric imaging. Multiple bandwidths and the colors associated therewith are collected for each point on the tooth, rather than a single red, or green, or blue bandwidths. Additionally, because calorimetric imaging uses monochrome sensors having non-colored pixels, no defects attributable to poor color fidelity affect the collection of bandwidths. The resultant image created with colorimetric imaging is an extremely accurate representation of the true colors of the tooth to be replaced. Moreover, dental prosthesis created from this color data is much more likely to match the color of the replaced tooth.

In another aspect of the invention, the optical measuring instrument includes a multi-functional sanitary shield. In addition to preventing contamination from spreading from one patient to the next, these shields are of a predetermined length to establish an optimal distance between (a) the illumination source and/or (b) the image sensor, and the object measured. The shield also includes a reference strip, preferably off-white, that is included in images collected by the optical measurement instrument. The value of measurement associated with this reference strip in collected images is compared during measurement to values acquired during instrument calibration. This comparison provides a method of determining not only the lamp intensity variation—and the illumination in general—but also provides a method to determine changes in lamp color temperature. Both of these values are used to provide accurate color measurement data from the imaged tooth. In a preferred embodiment, the disposable shield is also constructed from an opaque material that prevents any ambient light from entering the shield and affecting any measurements made by the optical measurement instrument.

In another aspect of the invention, the optical measurement instrument is configured so that an operator of the instrument may view an image of an object on a display, preferably a liquid crystal display (LCD), along a line of sight that is the same as the line of sight along which an image sensor of the instrument collects an image of the object. Accordingly, the operator views the object from the same perspective as the image sensor collects the image of the object. With this "line of sight" viewing, the operator may align the image sensor of the optical measurement instrument so that it collects the exact image she desires simply by looking at the LCD. She need not look at the object she desires to measure and then turn her head to view a separate monitor to confirm that what she expected the sensor to collect is what is actually collected.

In another aspect of the invention the optical measurement instrument includes a sealed housing that facilitates sanitation and cleanup. The housing is sealed at all joints of adjoining panels that make up the housing. An LCD display is sealably incorporated into the housing. Preferably the display is touch sensitive so that buttons and their corresponding apertures in the housing body are eliminated. The housing body also includes an aperture through which optical measurement illumination and sensing is performed. This aperture is covered with a transparent window that is sealably mounted to the housing. Because the housing and this aperture are sealed from the environment, the sensitive illumination and sensing instrumentation therein is not subject to pollutants such as dust or sanitizing or cleaning agents and the like.

In another aspect of the invention, the optical characteristics of a manufactured prosthetic restoration is compared to the optical characteristics of the damaged tooth that the restoration is to replace before the restoration is shipped to a dentist for installation in a patient's mouth. In the preferred embodiment, a dentist collects an image of a damaged tooth or remaining surrounding teeth with an optical measurement instrument. This image is electronically forwarded to a dental prosthesis manufacturer who subsequently creates a prosthesis, or restoration, to replace the damaged tooth. Before shipping the prosthesis to the dentist, however, the manufacturer uses her own optical measurement instrument to collect an image of the prosthesis, and compares this image to the original image of the tooth. During comparison, the manufacturer insures that the optical characteristics of the image of the prosthesis accurately duplicate the optical characteristics of the image of the tooth. If characteristics are satisfactory, the manufacturer ships the prosthesis to the dentist for installation in the patient's mouth. If the characteristics of the prosthesis do not satisfactorily match the damaged tooth or surrounding teeth, a new prosthesis is made, and its image is collected and compared to the image of the damaged tooth or surrounding teeth. This process may be repeated until a satisfactory prosthesis is created.

By insuring that the optical characteristics of a prosthetic restoration accurately match the optical characteristics of the damaged tooth, dentists and patients can be assured that when the prosthesis arrives from the manufacturer, it will be a satisfactory match of the damaged tooth and acceptable for installation in the patient's mouth.

In the discussion herein, reference is made to an "object," "material," "surface," etc., and it should be understood that in general such a discussion may include teeth, dentures, gums, other prosthesis or restorations, dental cleaning material, dental adhesives or the like or other dental objects as well as any other objects or materials as the "object," "material," "surface," etc.

These and other objects, advantages and features of the invention will be more readily understood and appreciated by reference to the detailed description of the preferred embodiments and the drawings.

DETAILED DESCRIPTION OF THE PREFERRED EMBODIMENT

Figure 6:
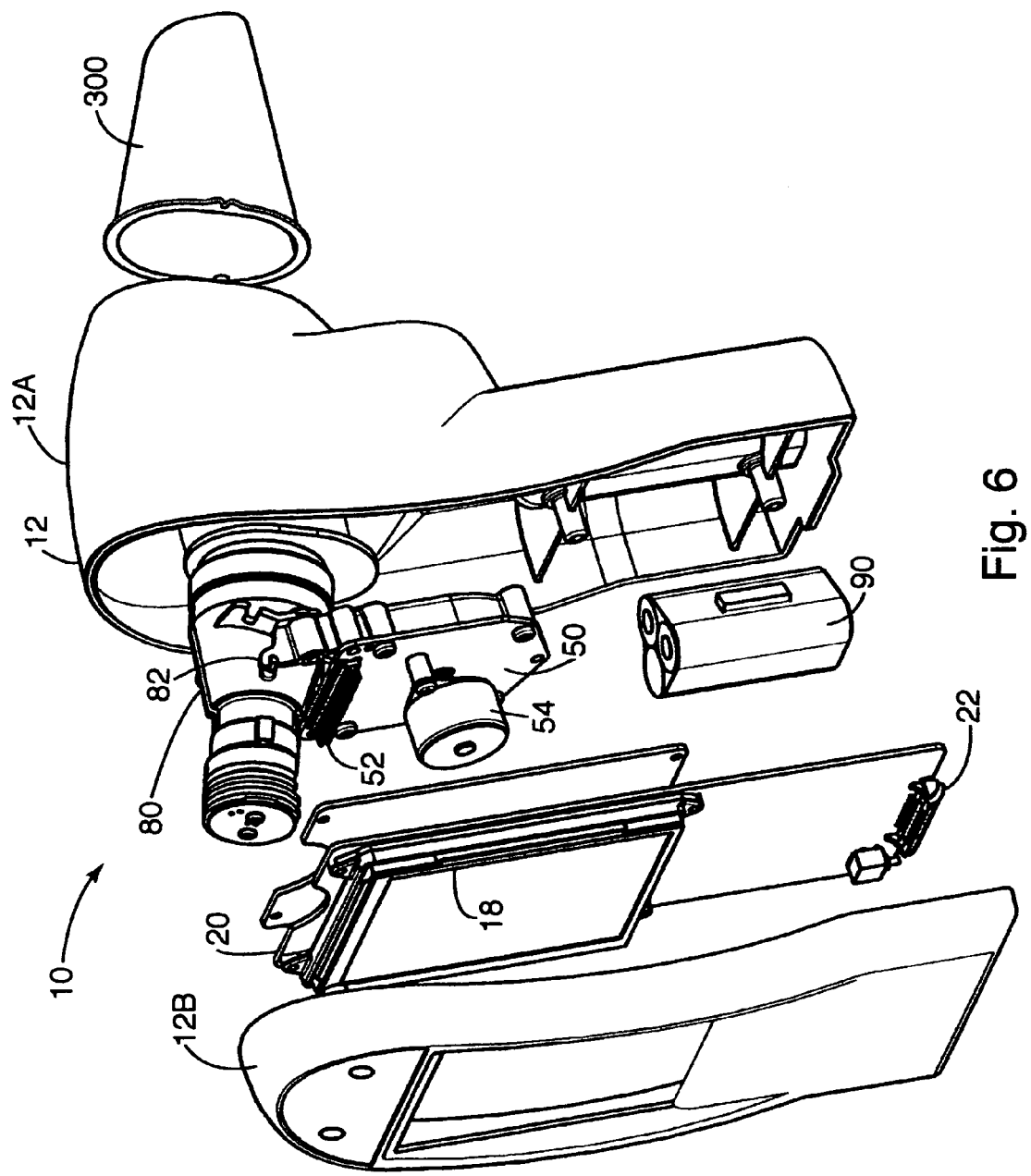
FIG. 6 is an exploded perspective view of an optical measurement instrument.

With reference to FIG. 6, the preferred embodiment of the optical measurement instrument 10 will now be described. The optical measurement instrument 10 generally includes a housing 12, display 18, processor 20, imaging subsystem 50, illuminator 80, power source 90, and sanitary shield 300. The housing 12 includes subparts 12a and 12b to allow easy assembly and access to the internal components housed therein. The housing subparts seat and seal together to create a housing that prevents contamination of sensitive internal components by dust and chemicals. The housing 12 may be constructed of any material; however, a light, easily cleanable, synthetic material, such as plastic, is preferred for handheld use and shock resistance.

The display 18 and the processor 20 may be separate or integrated as a unit as depicted. The display 18 is preferably a liquid crystal display (LCD). The LCD preferably has a touch screen interface to provide image control, data display and targeting feedback through a video viewfinder. As will be appreciated, any other display screens may be used. Alternatively, the optical measuring instrument may be connected via a cable (not shown) to a monitor or display (not shown) that is separate from the instrument for displaying images collected by the instrument.

In the preferred embodiment, the processor 20 is in electrical communication with the display 18, illumination assembly 80, and imaging subsystem 50. This processor is capable of processing digitized data collected from the imaging subsystem 50 and formatting it so that an image of that digitized data is output to the display screen 18. The processor preferably formats digitized measurements such as tristimulus value bandwidths collected by the image sensor 56 to form an image of the object measured on the display 18.

The processor 20 includes port 22 to connect to the instrument 10 to docking station, described in further detail below, to download images and/or data collected by the optical measuring instrument to a computer connected to the docking station for further analysis. Port 22 is also in electrical communication (not shown) with power source 90 so that the power source may be recharged when the instrument 10 is in its docking station.

Illuminator 80 is preferably mounted in the housing 12 in fixed relation to the imaging subsystem 50. This is accomplished via connectors 82 that may be of any configuration to hold the two assemblies in fixed relation. The fixed relation is preferably configured so that the illuminator 80 illuminates an object, such as a tooth, with light at a selected angle and the light reflected from the tooth is collected by the imaging subsystem 50 at a selected angle. In a preferred embodiment, the illuminator illuminates an object in an angle 18 degrees off normal and the imaging subsystem 50 collects light reflected from the object at an orientation normal to the object's surface. This configuration helps to reduce glare artifacts.

Of course, the illuminator 80 and imaging subsystem 50 may be configured in any angular configuration depending on the desired application. For example, the illumination and image capturing may be done both normal to the tooth. As will be also appreciated, the relation between the illuminator assembly 80 and imaging subsystem 50 may be configured such that with a combination of a beam splitter as known in the art, illumination and captuir of light reflected from an object may be done normal to an object's surface.

As will be appreciated, other conventional illumination assemblies may be substituted in the optical measurement instrument as the application requires. The assemblies may also include polarizers that limit the effect of specular gloss in the captured image.

Searchlight Illumination

Figure 7:
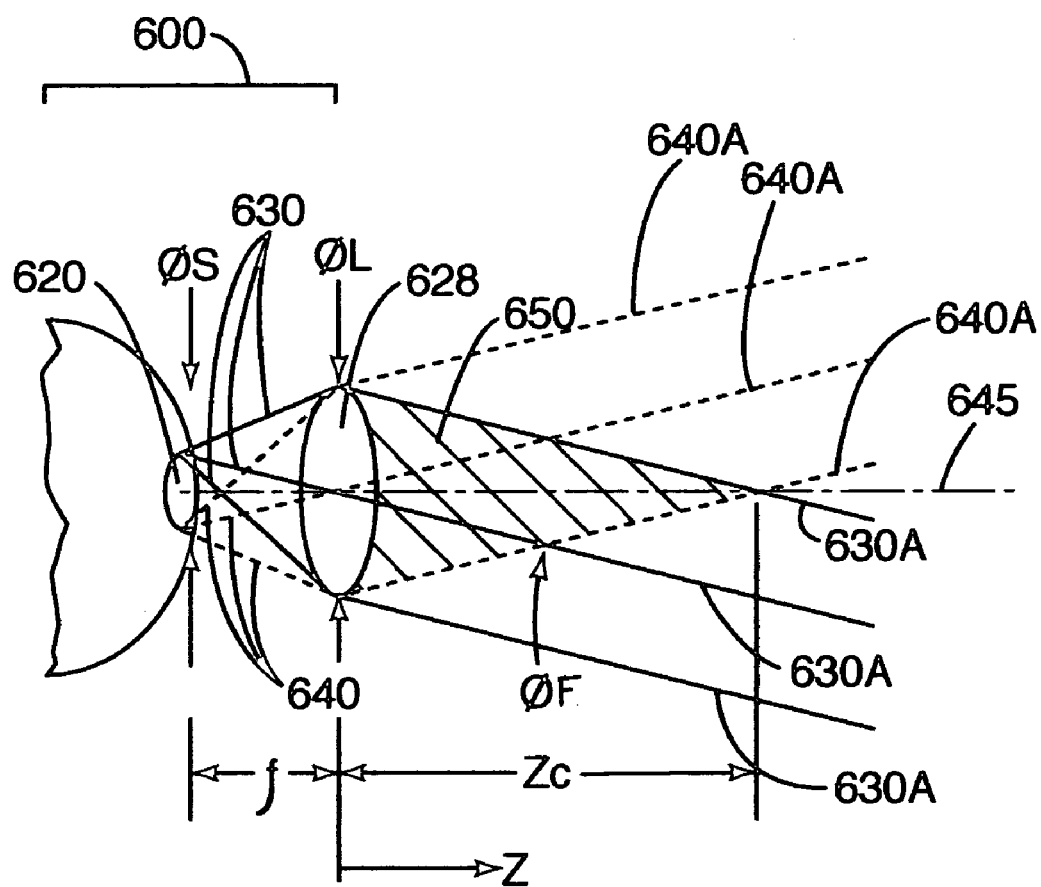
FIG. 7 is a side view of a region of constant irradiance.

The preferred embodiment of the optical measuring instrument uses searchlight illumination to illuminate objects during optical characteristic measurements. As used herein, "optical characteristics" means characteristics such as color, shade, translucence, gloss and/or shape. "Searchlight illumination" means illumination wherein the object measured is illuminated with constant irradiance. This definition is more readily understood with reference to FIGS. 7 and 8. FIG. 7 illustrates the constant irradiance phenomenon explained by J. Scheuch in his article, *Modeling of Constant Irradiance Illumination System*, pp. 22–27, SPIE Vol. 3428 (1998), hereby incorporated by reference.

As explained, FIG. 7 depicts a collimated uniform light source 600. The diameter of the integrating sphere exit port 620 is referred to as $\varnothing_S$, while $\varnothing_L$ refers to the diameter of the collimating optic 628, here, a thin lens. The effective focal length of the optic is referred to as f. Any point on the exit port of the integrating sphere 620 will produce a flux of collimated rays 640a and 630a to the right of the lens 628. The original light flux 630 and 640, formed by the top and bottom edges of the exit port 620 are shown. The shaded triangle 650 to the right of the lens 628 represents the region, or cone, of uniform irradiance. Although depicted as a two dimensional triangle, it will be appreciated that the region is actually a three-dimensional cone. Of course, depending on the aperture 620 and lens 628, the region of constant irradiance may take on cones of different shape as desired. At any point within this region 650, normal to the optical axis 645, irradiance will be a constant value. At points outside of the cone, the irradiance will fall off as the distance from the cone increases. The paraxial distance from the lens to the tip of the cell is referred to as the critical distance $Z_c$ and is given by:

$$Z_c = \frac{f\varnothing_L}{\varnothing_S} \quad (2)$$

At any point z along the optical axis where $z<z_c$, the diameter of the uniform field $\varnothing_F$ can be approximated by:

$$\varnothing_F = \frac{(z_c - z)\varnothing_L}{z_c} \quad (3)$$

Figure 8:
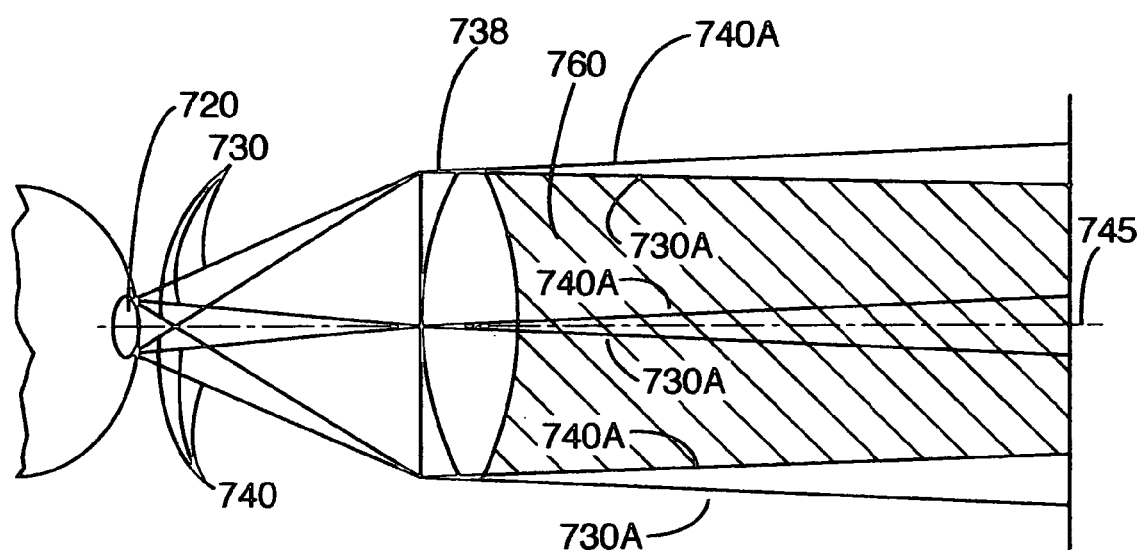
FIG. 8 is a side view of a modified region of constant irradiance used in searchlight illumination.

The region of uniform irradiance can be extended in length along the optical axis 745 as illustrated in FIG. 8. By positioning the exit port 720 at the focal of the achromatic doublet lens 738, the region of uniform irradiance 760 may be extended a substantial distance along the optical axis 745, as discussed in further detail below.

Figure 9:
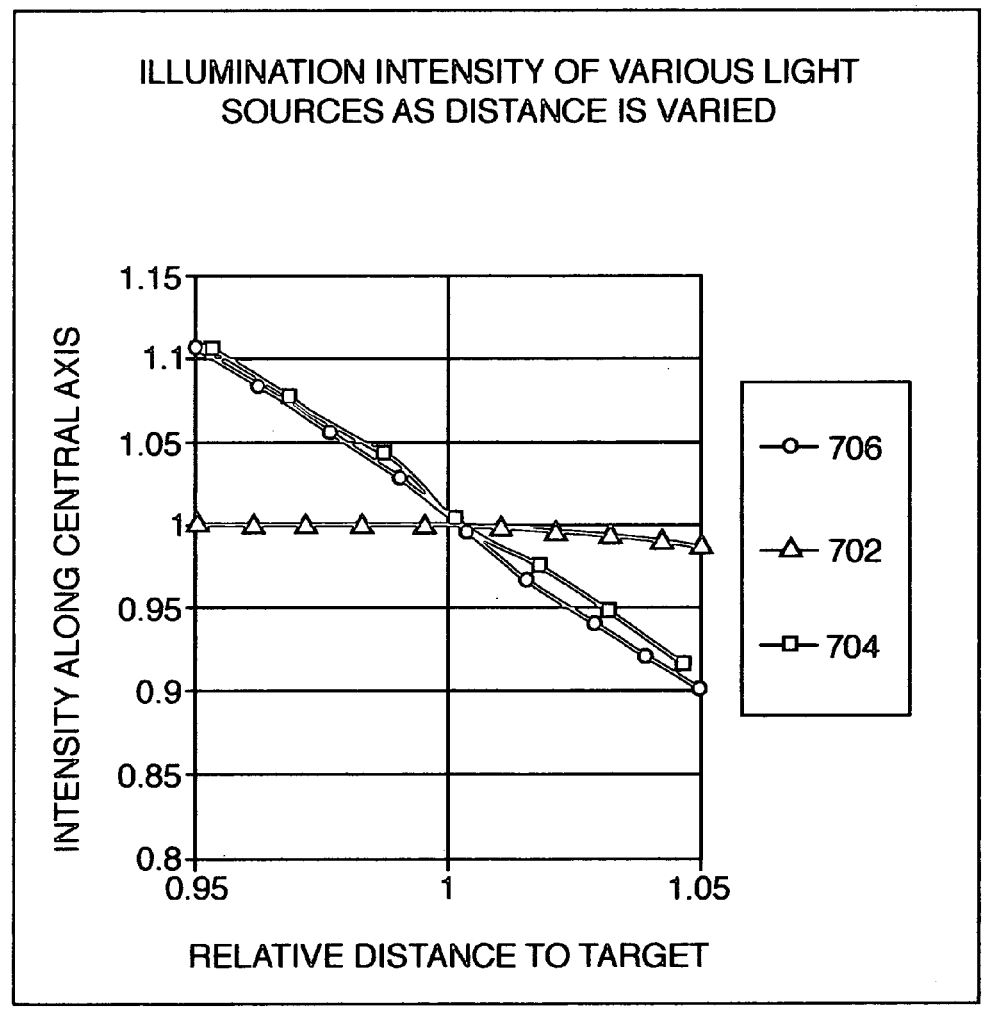
FIG. 9 is a graph comparing illumination intensity of various light sources as relative distance to an object is varied.

The advantage of searchlight illumination over conventional illumination techniques is illustrated in the graph of FIG. 9, entitled "Illumination Intensity of Various Light Sources as Distance is Varied." This graph illustrates the illumination intensity along the central axis from (a) a theoretical point source illumination 706, (b) conventional fiber optic illuminator 704, and (c) a searchlight source 702 used in the preferred embodiment. In the graph, the Y axis represents light intensity along a central axis of the illumination sources projecting in the same inaction as the light is projected. The X axis represents the relative distance from the target, that is, the object measured, to each source.

As shown, the intensity along the central axis from the theoretical point source 706 and fiber optic illuminator 704 is very strong when the target is near these sources; but that intensity rapidly decreases as the relative distance from the source to the target increases. In contrast, with a searchlight illuminator 702, which, by definition, has constant irradiance, the intensity along the optical axis remains substantially uniform at a distance within the operating range of the illuminator, as depicted by example here, from a relative distance of about 0.95 to about 1.0. At a distance somewhat greater than 1.05, the intensity from the searchlight gradually begins to decrease; but at a rate much less than the theoretical point source 706 and the conventional fiber optic illuminator 704.

Of course, as the illumination source distance to target is significantly increased (not shown on graph), even the searchlight illumination intensity will begin to decrease along the optical axis. But, for purposes of the carrying out the preferred embodiment of the present invention, illuminated targets or objects are positioned at a pre-selected distance from the searchlight source so that they are substantially within the region of constant irradiance.

The graph of FIG. 9 and related data are exemplary only; targets placed at different relative distances from the light sources may be illuminated by the searchlight source differently than as depicted. Moreover, even though the illumination intensity apparently decreases for searchlight sources along a central axis at relative distances greater than about "1," an object disposed at relative distances greater than 1 still may be considered to be illuminated within the region of constant irradiance. As used herein with reference to the present invention, "constant irradiance" means irradiance (or light) that is substantially uniform in intensity in three dimensions; the X and Y dimensions, and the Z dimension, which is preferably axially aligned with the central axis of a source of light. As used herein with reference to the present invention, "substantially uniform" means that the light preferably varies about ±4% in any of the three dimensions, more preferably about ±2% in any of the three dimensions, and most preferably about ±1% in any of the three dimensions.

Figure 1:
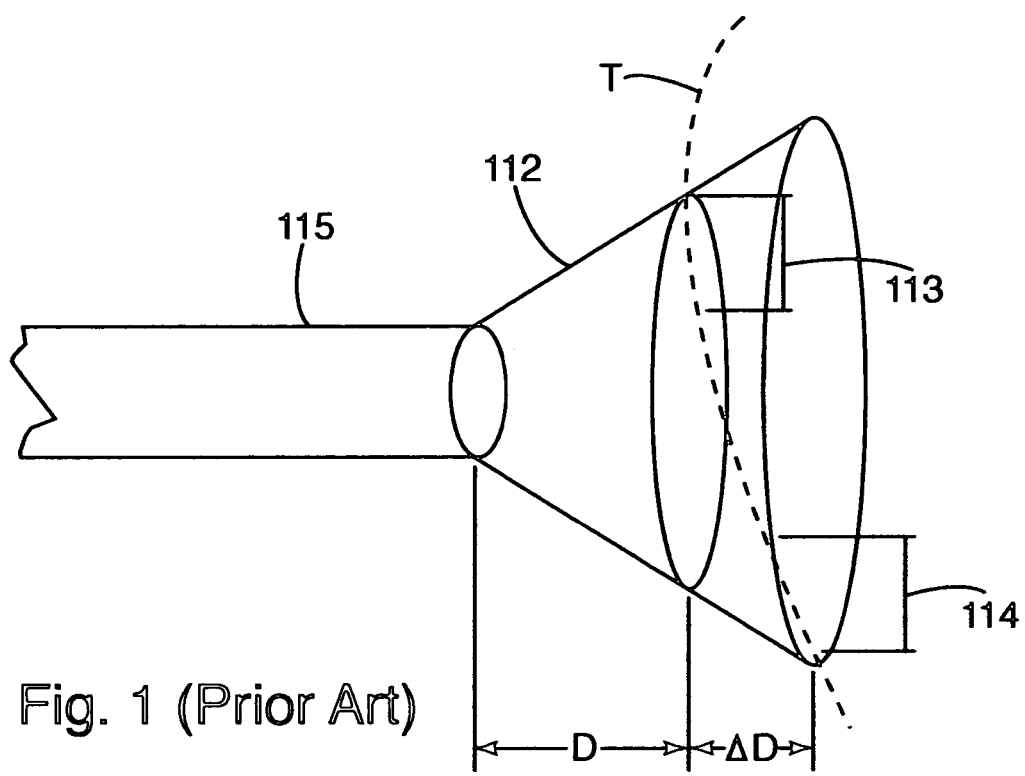
FIG. 1 is a side view of the intensity of light projected from a fiber optic illumination source of the prior art.
Figure 2:
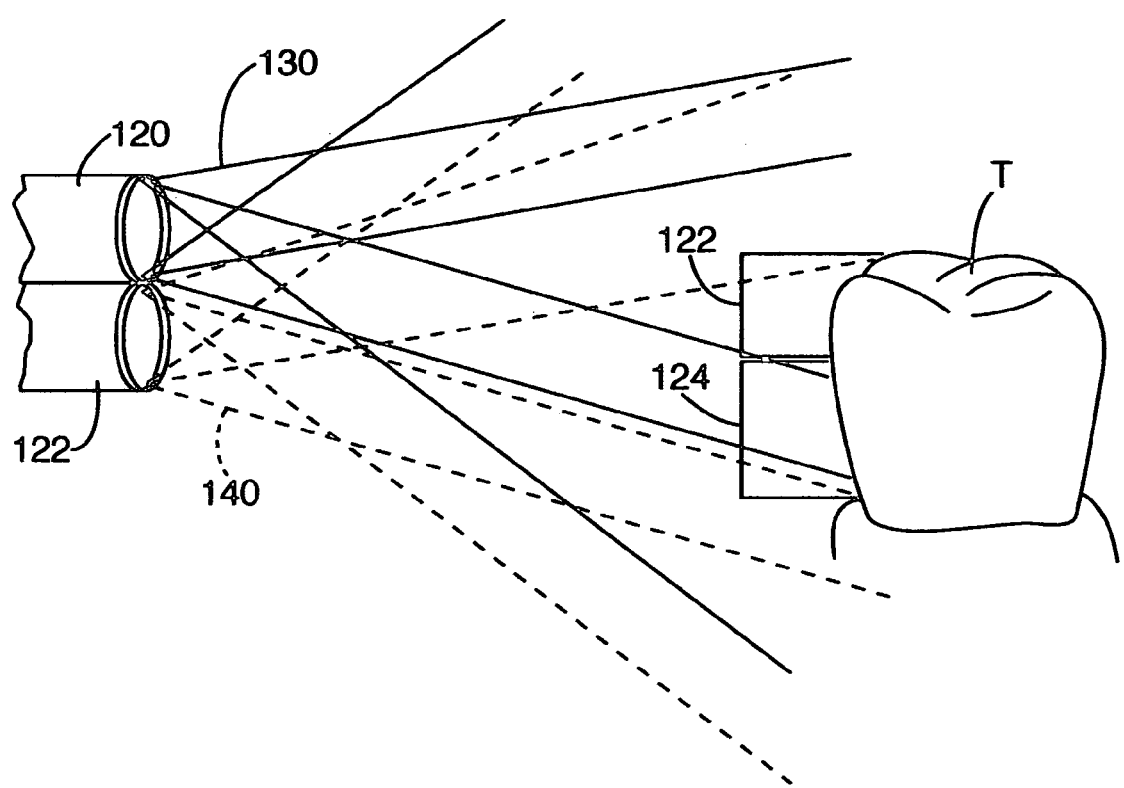
FIG. 2 is a side view of non-uniform illumination from a fiber optic illumination source of the prior art.
Figure 3:
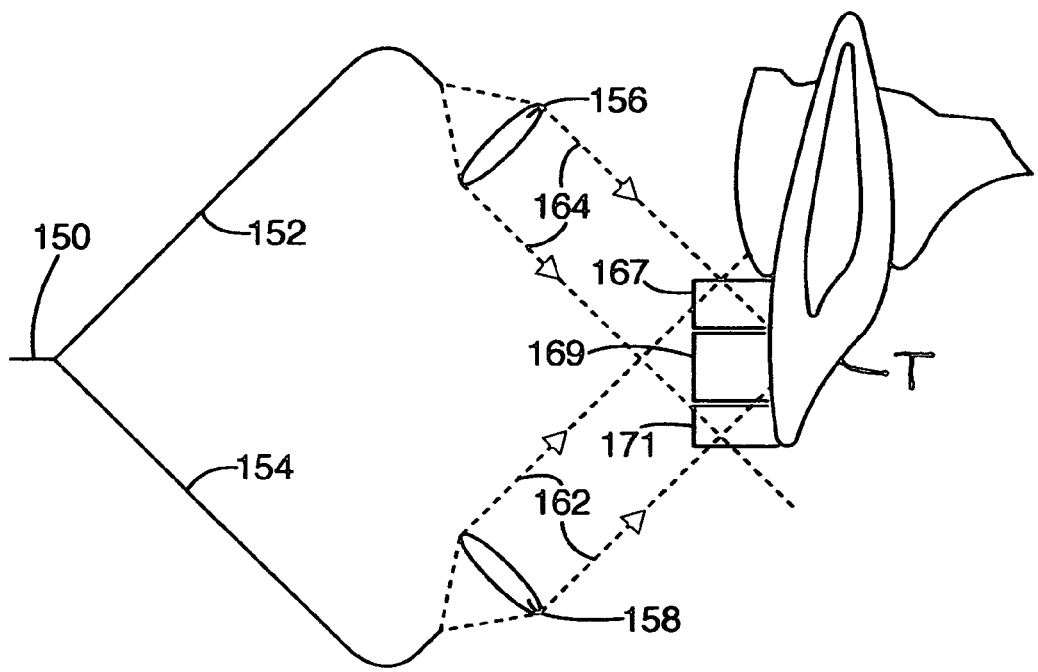
FIG. 3 is a side view of non-uniform illumination from a bifurcated fiber optic illumination source of the prior art.
Figure 4:
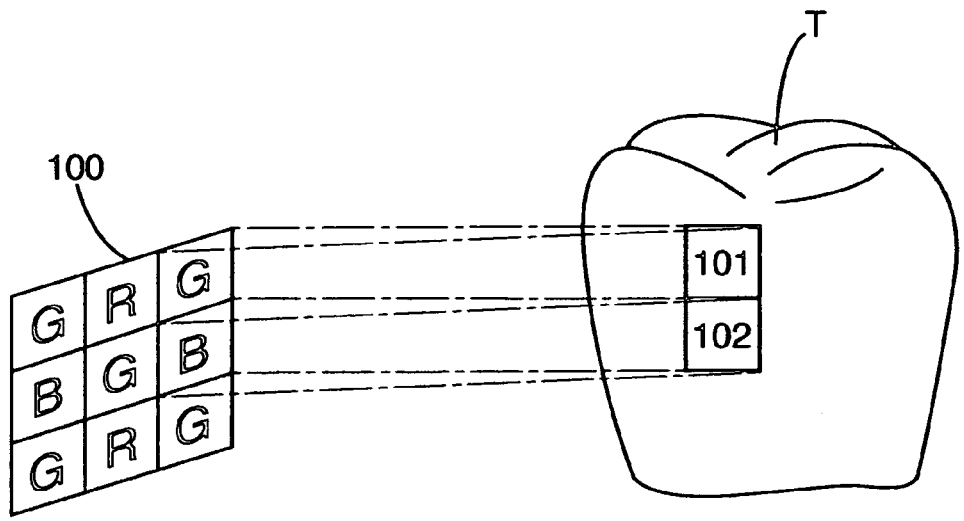
FIG. 4 is a perspective view of an RGB sensor of a prior art intraoral camera collecting color data from a tooth.
Figure 5:
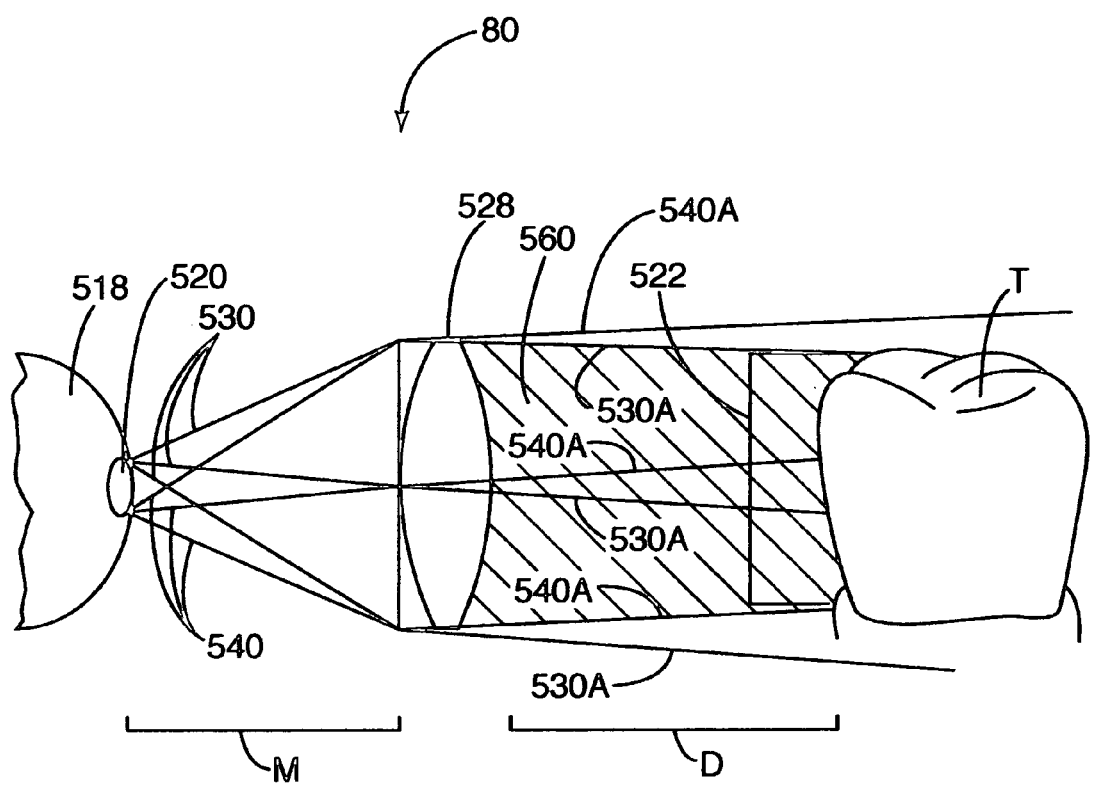
FIG. 5 is a side view of a the generic searchlight illuminator of the present invention.
Figure 10:
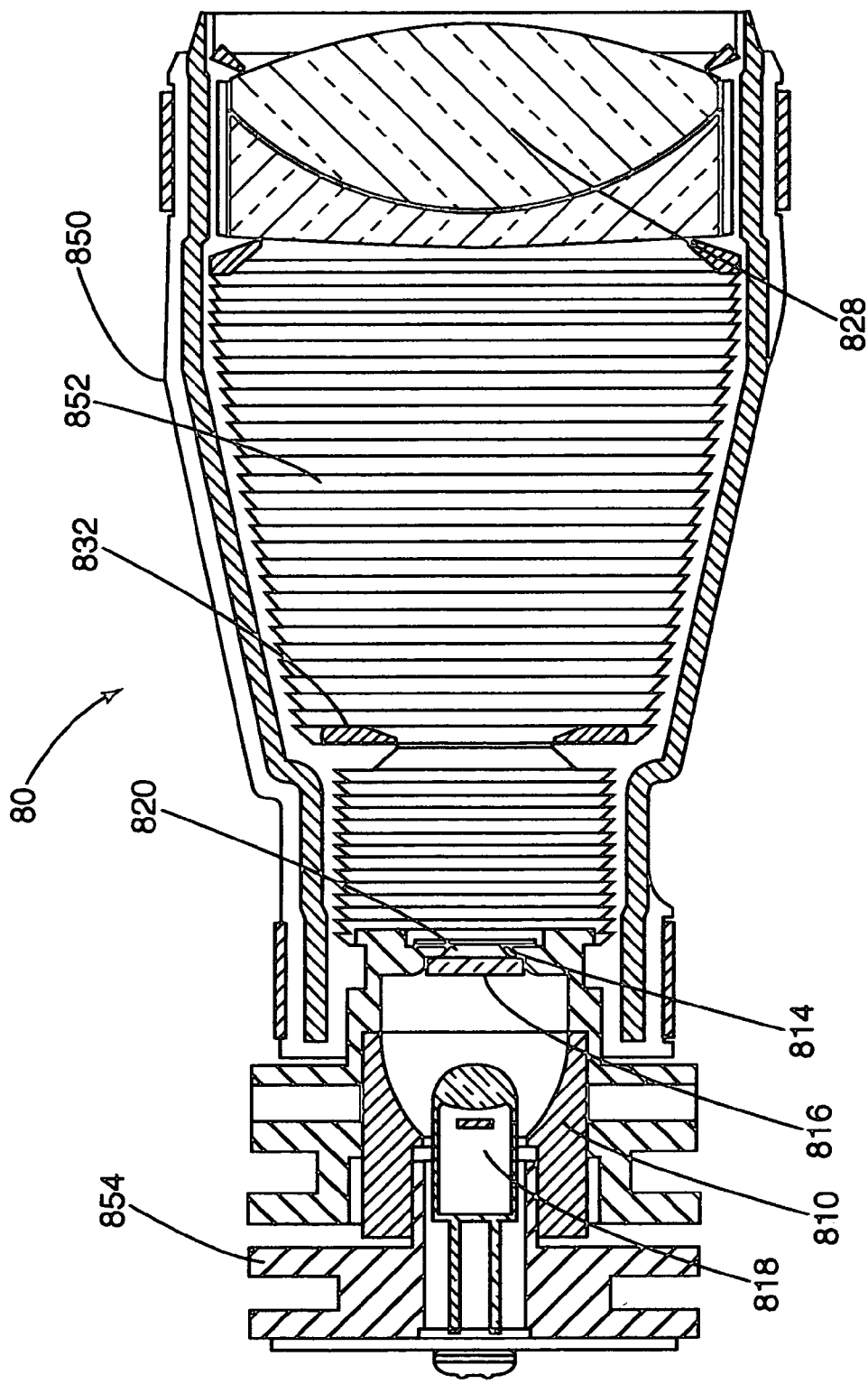
FIG. 10 is a sectional view of a preferred illuminator.

The optical measuring instrument of the preferred embodiment uses searchlight illumination to illuminate an object while the object's optical characteristics are measured. FIG. 5 generally depicts a searchlight illuminator and FIG. 10 depicts the searchlight illuminator as it is configured in the preferred embodiment of the optical measurement instrument.

With reference to FIG. 5, light fluxes 530 and 540 any projected through exit port 520 of illumination source 518 which is depicted as an integrating sphere, but may be any uniform diffuse source. The light fluxes are projected onto lens 528 positioned at a pre-selected distance M from the illumination source 518. Depending on the desired size of the region of constant irradiance 560, this distance M is experimentally determined. The light fluxes 530 and 540 transmitted through lens 528 form a region of constant irradiance 560 including transmitted light fluxes 530a and 540a. The lens may, of course, be of any configuration capable of forming regions of constant irradiance and need not be limited to the achromatic doublet lens depicted.

The searchlight illuminator 80, including source 518 and lens 528, preferably is placed a pre-selected distance D from the center of the object for which optical measurements are to be collected. The center of the nominal object or target may be placed at about 50 millimeters to about 100 millimeters from the lens, preferably from about 60 millimeters to about 70 millimeters from the lens, more preferably from about 63 millimeters to about 67 millimeters from the lens, and most preferably, about 65 millimeters from the lens. This distance D establishes a reference distance within which all points of the object optically measured are illuminated in the region of constant irradiance 560. For purposes of taking optical measurements of teeth, it is preferable to illuminate a substantial portion of the tooth or remaining teeth with the region of constant irradiance 560.

To establish distance D and insure that the points of the object measured are within the region of constant irradiance, a spacer is used to separate the illuminator 80 from the tooth. Preferably, a sanitary shield, described in further detail below, is attached to the optical measuring instrument that includes illuminator so that when the shield is disposed against or adjacent to the tooth, the distance D is established and the tooth is positioned in the region of constant irradiance. As will be appreciated, the illuminator 80 is positioned so that the light of the region of constant irradiance is reflected and detected by the imaging subsystem of the preferred optical measuring instrument described in further detail below.

With reference to FIG. 10, the preferred configuration of the illuminator 80 will now be described. The illuminator 80 generally includes light source 818 that is preferably a halogen lamp that emits white light. Of course, any conventional lamp, bulb or uniform and diffuse light source may be used depending on the desired application. Preferably, the light source 818 is incorporated into a sub-housing 854 that is removable from main housing 850 so that the light source 818 may be replaced or serviced. Focusing reflector 810 focuses light from the light source 818 through aperture 820 so that light rays are projected onto lens 828. Optionally, the aperture 820 may include adjacent to it a light shaping diffuser 816 that provides even light distribution and homogenizes light fluxes to provide uniform application in transmission of light from the light source 818 to the lens 828. The preferred light shaping diffuser is available from Physical Optics Corporation of Torrance, Calif. Of course, any diffuser capable of homogenizing and/or enhancing the uniformity of light transmitted from a light source to a lens may be used.

Light rays from light source 818 are projected through aperture 820 whose size is determined by the desired application and distribution of searchlight illumination by the illuminator 80. The aperture optionally may be covered by heat absorber 814 which is preferably in the form of a heat absorbing glass plate or synthetic material. The heat absorber 814 absorbs excessive heat created by the light source 818. Of course, this heat absorber 814 may be omitted in applications where there is no concern of heat buildup.

Illuminator 80 also includes a light limiting stop 832 that precisely configures the light from the aperture 820 on the lens 828. As will be appreciated, optical back scatter fins 852 are included in the housing 850 to prevent excessive back scatter of light that may confound the light transmitted by the light source 818 to the lens 828. Of course, the fins 852 may be colored, such as with a black or dark color to further reduce back scatter of light.

The illuminator housing holds lens 828 a predetermined distance from light source 818 to optimize the searchlight illumination projected from the illuminator 80. Of course, as discussed above in reference to FIG. 5, the distance from the lens to the light source may be varied to obtain the desired searchlight illumination. The lens preferably is an achromatic doublet lens, but as will be appreciated, any lens capable of providing a region of constant irradiance at significant distances along the optical axis of the lens may be used.

With reference to FIG. 6, the illuminator 80 is configured in fixed relation to the optical imaging subsystem 50 so that the illumination reflected from the object measured is reflected back to the imaging subsystem 50 for sensing and subsequent measurement of optical characteristics of an object. In operation, the illuminator depicted in FIG. 10 performs in the same manner discussed above in reference to the generic illuminator of the present invention depicted in FIG. 5.

Imaging Subsystem

Figure 11:
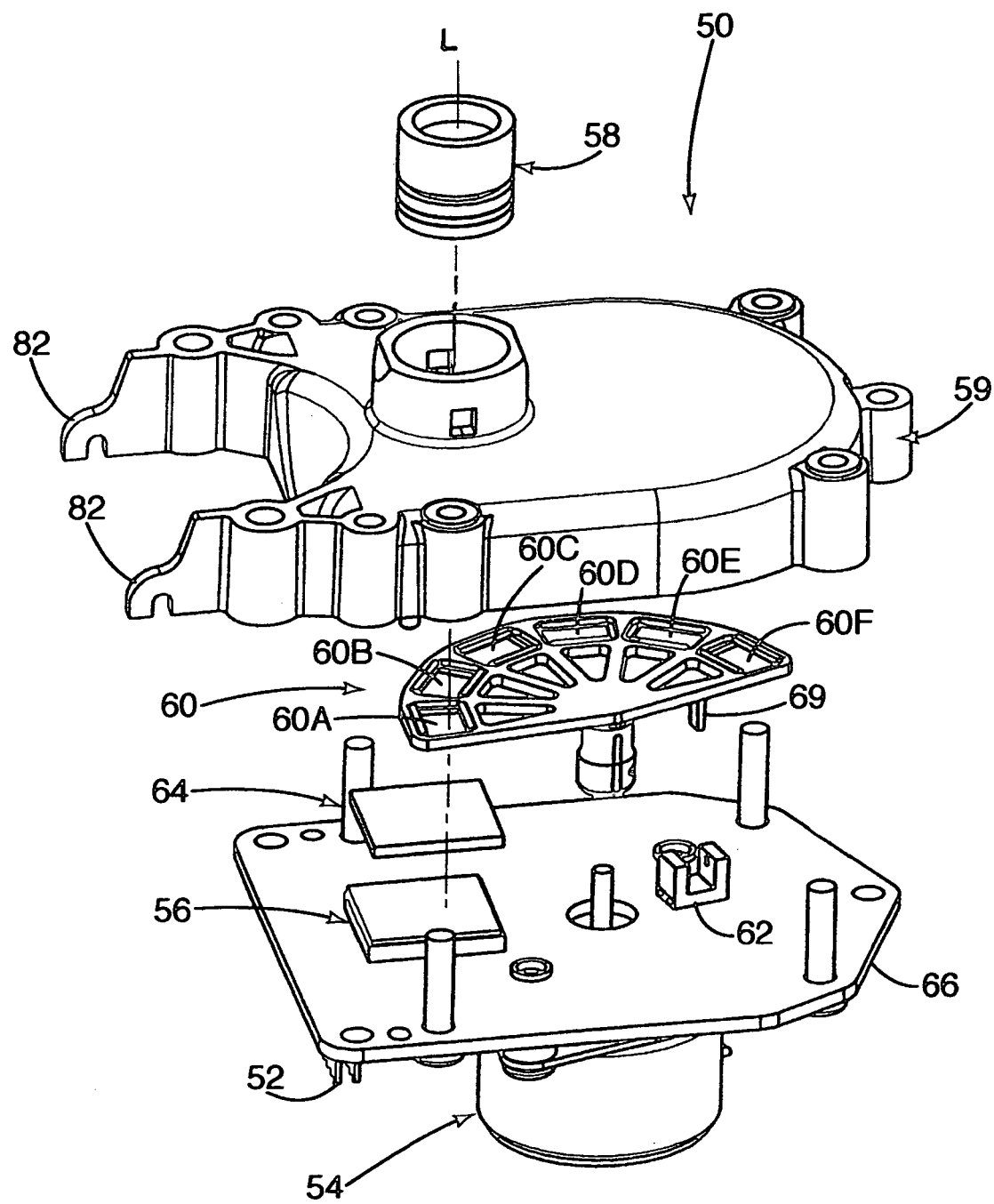
FIG. 11 is an exploded perspective view of an imaging subsystem.

With reference to FIGS. 6 and 11 in the imaging subsystem 50 will now be described. The imaging subsystem is in electrical communication with the processor 22 to enable transfer of optical characteristic data in digitized form collected by the imaging subsystem 50 to the processor 20. The electric prongs 52 may be connected to a cable (not shown) that provides this electrical communication with the processor 20. Additionally, the connector 52 may be connected to an additional cable (not shown) that provides electrical communication with the power source 90 to enable the operation of motor 54 and image sensor 56 depicted in FIG. 11.

With particular reference to FIG. 11, the preferred imaging subsystem includes lens 58 mounted in cover 59; filter wheel assembly 60 rotatably mounted to and driven by stepper motor 54 which is mounted to support plate 66; position sensor 62 for indexing rotation of the filter wheel 60, and image sensor 56. The subsystem may optionally include an infrared blocking lens 64 to prevent infrared bandwidths from reaching the image sensor. All of these elements arranged so that light L, reflected from a tooth is transmitted through lens 58, one of the filter elements 60a–f, and the infrared blocker 64, ultimately impinges on and is captured or collected by the image sensor 56. The image sensor 56 converts this light L to digitized form and transfers the digitized form to processor 20.

Alternatively, the imaging subsystem may be configured so that the filter assembly is positioned between an illumination source and the object measured (not shown). In this manner, light from the illumination source would be transmitted through the filter assembly elements before being reflected from the tooth; however, reflected light impinging on the image sensor would still be of bandwidths selectively transmitted by the filter elements.

The lens 58 preferably has low chromatic aberration over the visible light spectrum from the 380 nm to 700 nm wavelength range. The lens focuses light L toward the image sensor 56, and causes the light to be transmitted through the elements of the filter wheel 60a–60f in the process. The filter wheel assembly of the preferred embodiment is a sector of 180 degrees including six elements. Of course, the assembly may be of any shape and include any number of filter elements.

The filter wheel assembly 60 of the preferred embodiment includes filter elements 60a–f, wherein filter elements 60a–d are of pre-selected band pass functions. "Band pass function" means information that is used to specify how a filter absorbs specific wavelengths of light as that light, also referred to as "radiant flux," is transmitted through a material. More preferably, filter element 60a has a band pass function that permits it to transmit only X tristimulus value bandwidths and attenuate all other bandwidths; 60b has a band pass function that permits it to transmit only Y tristimulus value bandwidths and attenuate all other bandwidths; 60c has a band pass function that permits it to transmit only Z tristimulus value bandwidths and attenuate all other bandwidths; and 60d has a band pass function that permits it to transmit only X' tristimulus value bandwidths and attenuate all other bandwidths. These filters consistently attenuate bandwidths outside selected bandwidths to less than about $1/40^{th}$, preferably less than about $1/100^{th}$, and more preferably less than about $1/1000^{th}$ of the value of the maximum transmittance of the filter. Of course, the filter elements 60a–d may have any band pass function and attenuation as desired, and they may be altered in number so that only a selected number of filters are used in measurement.

Optionally, the filter assembly 60 may include opaque element 60e to establish dark current information of the image sensor 56. Dark current information is current that flows in an image sensor when no optical radiation is impinging on the sensor. This current effectively distorts the electronic signals transmitted by the sensor to the processor. Accordingly, it is preferred to measure this dark current information and subtract it from the electronic signals generated during collection of bandwidths transmitted to the sensor so that subsequent optical characteristic measurements do not include this dark current information. The filter wheel may also include an open element space 60f that transmits all light wavelengths to the image sensor. Transmitting all light wavelengths to the image sensor may be desired when initially acquiring an image of an object to help identify regions of the tooth that have high gloss.

With reference to FIG. 11, the filter is indexed with index 69 that interacts with position sensor 62 to synchronize the timing of imaging sensing by image sensor 56 and alignment of individual filter elements 60a–f over the image sensor 56. The position sensor may be a photodiode position sensor or any other sensor capable of sensing movement of the filter wheel 60 via detection of the position of index 69. The position sensor 62 is in electrical communication with the processor 20 so that the processor may initiate the stepper motor 54. Stepper motor 54 sequentially rotates the filter wheel assembly in pre-selected angular increments to position elements of the filter wheel 60a–60f over the image sensor so that light is transmitted through the light transmitting elements to the image sensor 56.

The stepped motor 54 is mounted to the back of the support plate 66 in a manner that limits contamination, magnetic field interaction, and heat transfer from the motor to the image sensor 56. The stepper motor preferably rotates the sectored filter wheel 60 in an indexed versus free-spinning manner.

The image sensor 56 is preferably a complimentary metal-oxide semiconductor (CMOS). As will be appreciated, any monochromatic sensor or photo detector may be substituted for the CMOS, including but not limited to a charged coupling instrument (CCD) sensor. As will be appreciated, the image sensor collects or captures bandwidths of the light L that is transmitted through respective filter elements 60a–d, converts those functions to digitized form, and transfers the digitized form, also referred to as electronic signals, to the processor 20.

The stepper motor 54 and image sensor 56 are all synchronized, preferably by the processor 20, so that the image sensor 56 collects the bandwidths transmitted through each filter element 60a–d when those filters are aligned one by one over the image sensor 56. The position sensor provides feedback via interaction with index 69 to the processor 20 to initialize and deactivate the stepper motor 54 in a desired manner.

With reference to FIG. 11, the preferred operation of the imaging subsystem will now be described. Light reflected from an object, preferably a tooth, travels pathway L through lens 58. Lens 58 focuses light reflected from the tooth toward the image sensor 56. In so doing, selected bandwidths of the light L is transmitted through one of the filter wheel elements 60a–f. Each transmission of light L through an individual filter, and each instance where no light is transmitted through the opaque element, and each instance when all light is transmitted through the open element is referred to as a "frame." The stepper motor 54 sequentially aligns each of the filter elements 60a–60d and optionally the opaque and open filter elements 60e and 60f, respectively, over the image sensor 56. The image sensor 56 collects a frame when each filter element is placed over the sensors. Accordingly, in the preferred embodiment, the image sensor 56 collects, frame by frame, different tristimulus value bandwidths that are transmitted through the elements of the filter wheel 60.

The alignment of elements 60a–f is controlled by stepper motor 54 which is controlled by processor 20. In the preferred embodiment, when color measurement of light L reflected from a tooth is initialized, the stepper motor is in a "park" mode; that is, index 69 is aligned with position sensor 62. During measurement, the processor directs the stepper motor to rotate from the park mode through a plurality of partial movements consequently turning the filter wheel assembly 60 a plurality of pre-selected angles. These angles are such that each filter wheel element 60a–60f is positioned over the image sensor so that image sensor 56 collects a frame of data for light transmitted through each of the filter elements individually or for dark current into motion when element 60e is positioned over the sensor. In this manner, only one bandwidth is transmitted to and captured by the image sensor at a given time or in a single frame.

In the preferred embodiment, the image sensor 56 takes three color measurements of a tooth. Each measurement comprises nine frames of data, which are subsequently stored in a processor 20 and combined to form a single measurement, or "image" of the tooth. Those frames represent two transmissions of X bandwidths of light L through filter 60a two transmissions of Y bandwidths of light L through filter 60b two transmissions of Z bandwidths of light L through filter 60c, two transmissions of X' bandwidths of light L through filter 60d, and a single dark current information frame when the opaque element 60e is positioned over the image sensor 56. This duplication of frames helps to integrate over time the collected bandwidths and may provide data needed for stabilization of the image.

As used herein, "stabilization" means combining the frames of data collected at different points in time so that the resultant image does not indicate that the optical measuring instrument was moved between the points in time during which the frames were taken. Multiple frames reflected by the sensor are separated in time because it takes a small fraction of time to collect a first frame, through, for example, filter element 60a, move the filter wheel assembly 60 with the stepper motor 54 and collect the next frame through, for example, filter element 60b. During this small fraction of time, the operator of the optical measurement instrument may accidentally move the instrument by rotating or shaking it. Accordingly, the frame collected for one filter element may be slightly different from other frames and the frames will not match up point for point. To correct this, once the data is converted to digitized form by the sensor and communicated to the processor, the processor uses special algorithms to align the frames so that a substantial number of points on one frame collected match up with a substantial number of points on the other frames collected.

Figure 12:
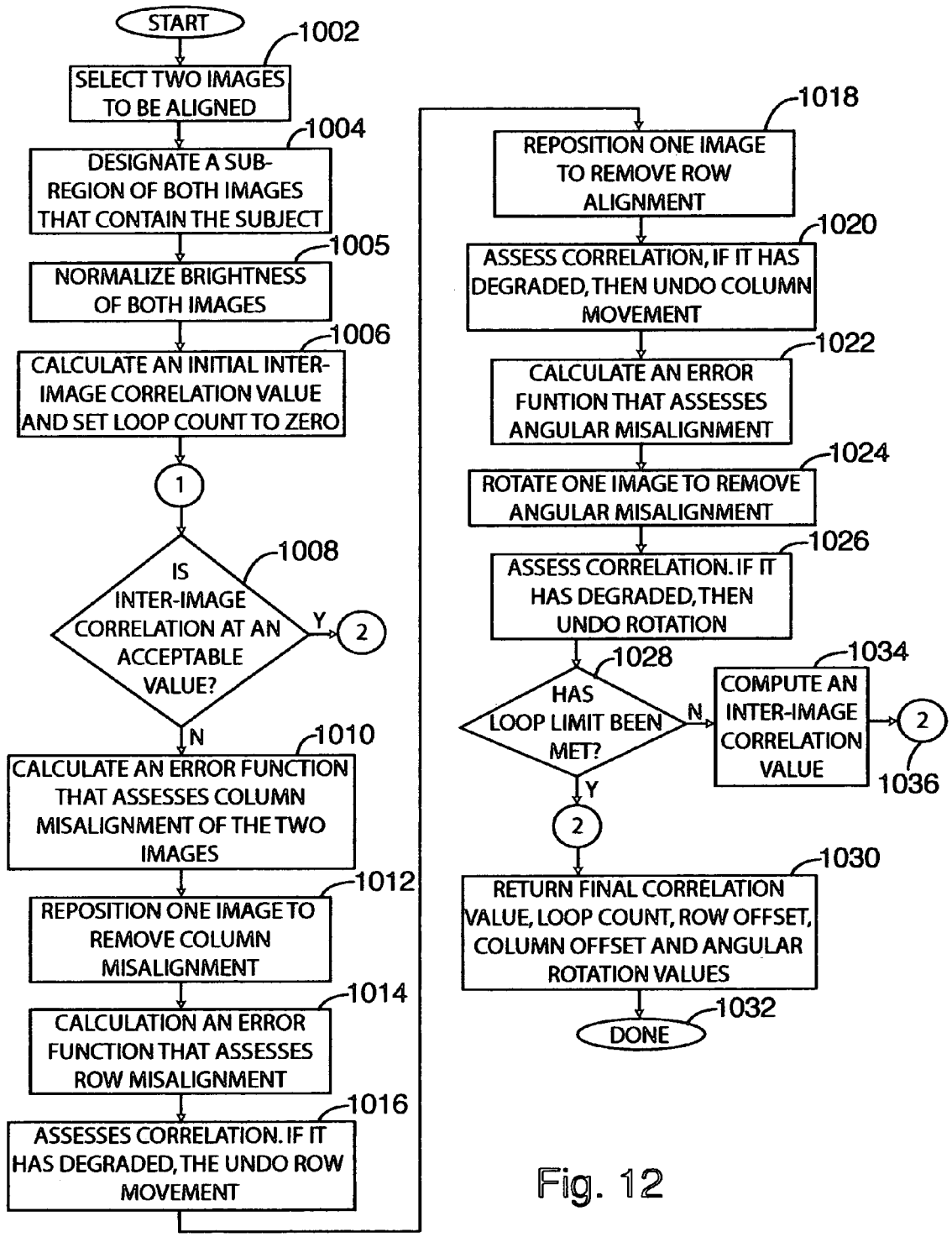
FIG. 12 is a flow chart of an alignment process of the imaging subsystem.

A flow diagram conceptually outlining the process of aligning frames is depicted in FIG. 12. This process is preferably carried out by the processor of the instrument, but may alternatively be carried out by a separate computer if desired. Aligning frames may begin with the selection of two or more images to be aligned 1002. A sub-region of both images containing the object desired is designated 1004. The brightness of these designated images are normalized 1005. An initial inter-image correlation value is calculated and a loop count is set to zero 1006. At macro step 1, a query is offered; is the inter-image correlation at an acceptable value 1008? If yes, the process skips to macro step 2 and step 1030 where it returns final correlation value loop count, loop count, row offset, column offset and angular rotation values. From this step, the process proceeds to done 1032.

If no is the response to query 1008, the process proceeds with step 1010, where an error function that assesses column misalignment of the two images is calculated. In step 1012, one image is repositioned to remove column misalignment. In step 1014, an error function that assesses row misalignment is calculated. In step 1016, correlation is assessed; if correlation has degraded, then row movement is undone. In step 1018, one image is repositioned to remove row misalignment. Correlation is assessed in 1020; if it has degraded, then column movement is undone. An error function is calculated that assesses angular misalignment in step 1024. In step 1026, correlation is assessed. If correlation has degraded, then the rotation is undone.

In step 1028, a query is offered; has the loop been met? If yes, the process skips to macro step 2, and 1030, where it returns to final correlation value loop count, loop count, row offset, column offset and angular rotation values. The process proceeds to being done 1032. In step 1028, if the response is no, a inter-image correlation value is computed 1034; and the process skips to macro step 1 again to repeat all steps as necessary any number of times so that the process proceeds to done 1032. Of course, the preferred process may be modified in sequence. Steps may be modified and/or selectively repeated. Different steps may be added as well, depending on the desired application.

When the points of each frame are aligned with all the points of all other frames, the frames are collectively displayed to form an image of the object that reflected the light collected by the sensor. Preferably, a substantial number, if not all, of the points of this image will include all the tristimulus value bandwidths, that is the X, Y, Z and X' tristimulus bandwidths that were collected by the image sensor. This image is preferably displayed on display 18 and stored in microprocessor 20. The image may be downloaded from the microprocessor 20 to a personal computer. In embodiments where only tristimulus bandwidths are collected by the imaging system, it will be appreciated that there is no need to perform lengthy calculations to derive tristimulus values if the output of the system be in tristimulus value format.

As will be further appreciated, the bandwidths collected by the image sensor may be combined and averaged in an image of the object into regions of uniform bandwidths. It is also possible to arithmetically combine into color zones those adjacent image points where color deviation between these adjacent image points do not exceed a predetermined value. In this way, measured tooth color can be subdivided into several color zones having different colors or bandwidths. The maximum number of such color zones in a prosthesis may be limited because a dentist or restoration manufacturer usually subdivides a prosthesis only into a limited number of color zones.

In addition to matching points to stabilize and/or align the frames to form an image of the tooth, the processor may also detect measurement errors if frames have been improperly collected. For example, if the operator of the optical measurement instrument drastically rotates or moves up and down or side to side the measuring instrument while sequential frames are being collected, one or more of the collected frames may be drastically different from the other. For example, one frame may be of a tooth and the next may be of a gum due to the drastic movement of the optical measuring instrument between frames. Accordingly, it would be difficult to align the points of one frame with the corresponding points of other frames because the frames would be quite different.

In cases where the processor detects that the frames collected are sufficiently different from one another so that corresponding points of different frames cannot be matched to form an image of the tooth, the processor indicates to the operator that the measurement must be redone. This indication may be communicated via display means or any other conventional alarm means. Accordingly, the operator retakes the optical characteristic measurement of the tooth to collect satisfactory data. As a result, the optical measuring instrument insures accurate and complete images are collected for further processing and manufacture of dental prosthesis.

Additionally, the processor preferably has the capability to store three or more images of object. These images may be recombined or welded together using appropriate welding software to combine multiple images into a single image. For example, dentists may use welding software to arrange individual images downloaded from the optical measuring instrument into a single image that replicates the configuration of teeth surrounding a damaged tooth in a patient's mouth.

Sanitary Shield

Figure 13:
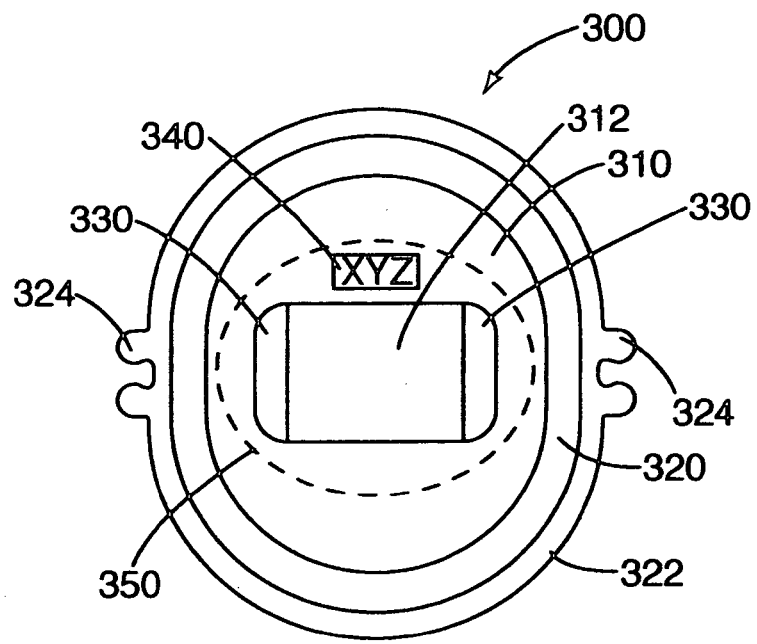
FIG. 13 is an end view of a sanitary shield.
Figure 14:
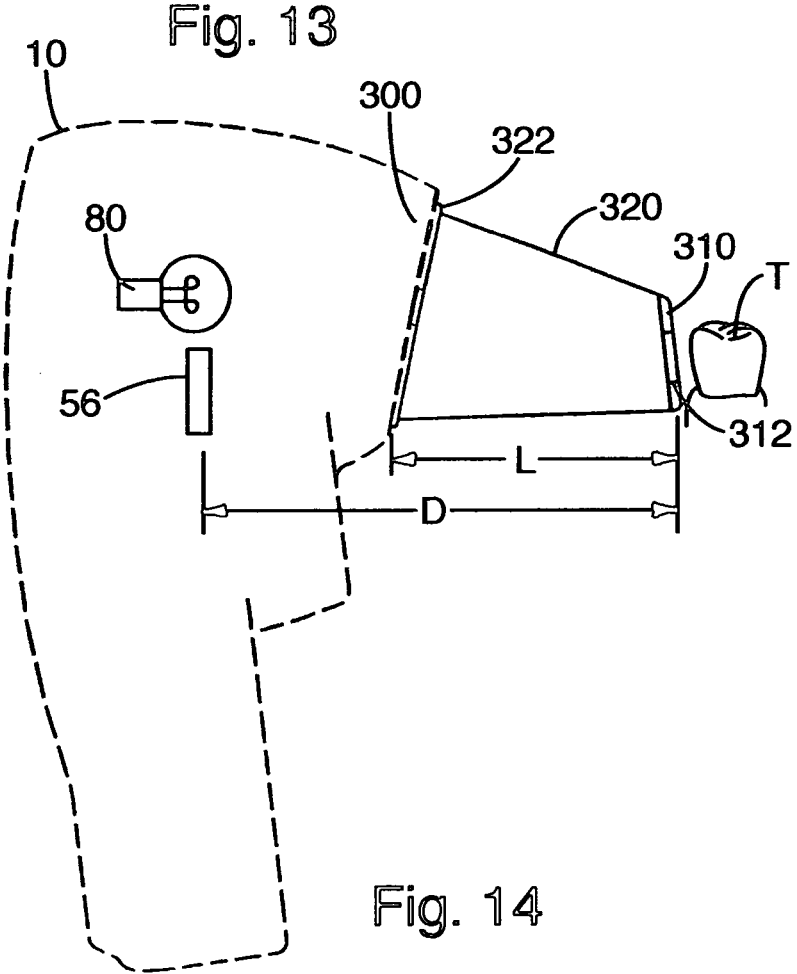
FIG. 14 is a side elevation view of the sanitary shield in use.

The shield used in conjunction with the preferred optical measurement instrument is generally depicted in FIGS. 13 and 14. The shield 300 is generally a hollow body having a tapered portion 320; however, the dimensions and size of the shield and its components may be varied for different applications. The shield is preferably hollow so that it freely transmits light through it, that is, first end 322 is in "illuminatory communication" with second end 310. Disposed at one end of the tapered portion is first end 310 that defines aperture 312. The aperture 312 may be of any size depending on the illumination source and the amount of light desired to be collected that is reflected from the object measured. Reference color strips 330 border the edges of the aperture. These strips are adjacent the aperture or at least positioned so that they are in the image field 350. The image field is the field that is included in an image that is collected by an image sensor of the optical measurement instrument. The reference strips may be included on the tapered portion 320 as long as they are included in collected images. Preferably, the color of the reference strips is off-white, but any color may be used, as long as the strip is of a known color.

In operation, the reference strip is included in the image field 350 when the optical measurement instrument collects an image of an object. The measured reference strip values are compared to values acquired during instrument calibration. This comparison provides a method of determining not only the lamp intensity variation, but also provides a method to determine changes in lamp color temperature. Both of these values must be known to provide accurate color measurement data from the imaged tooth. Lamp compensation factors are applied to all other objects in the image field 350, such as a tooth to determine the true colors of those objects. A true color image of the object may then be produced from these true colors.

The interior of the shield's hollow body is preferably opaque or otherwise colored with a dark material that prevents ambient light on the exterior of the shield from entering into the shield and polluting the data collected in the image field 350.

The shield 300 may also include indicia 340 disposed on first end 310. The indicia are preferably configured on end 310 so that it is included in the image field 350 when an image is collected. These indicia may be of any type, but preferably indicates the origin, such as manufacturer or distributor of the disposal shield to prevent counterfeiting thereof. The indicia 340 may also include patient information, a shield lot number, an expiration date, or any other information relevant to the patient or the optical measuring instrument. The indicia may be printed on, included in, affixed to or otherwise associated with the shield in any conventional manner. For example, the indicia may be a printed adhesive label or a barcode.

In the preferred embodiment, the shield establishes a predetermined distance to an object from an illumination source 80 or image sensor 56 as depicted in FIG. 14. The length of the shield L is pre-selected so that when aperture 312 is disposed adjacent to or in contact with the object to be measured, for example the tooth T, the illumination source 80 and image sensor 56 is a specific distance D from the object T. Accordingly, the precise illumination or sensing by the illuminator 80 or sensor 56 may be duplicated in every measurement. This specific distance is also pre-selected to prevent diffusion or scattering of the light generated by the illumination source 80 by the time the light reaches the aperture or object measured.

Figure 17:
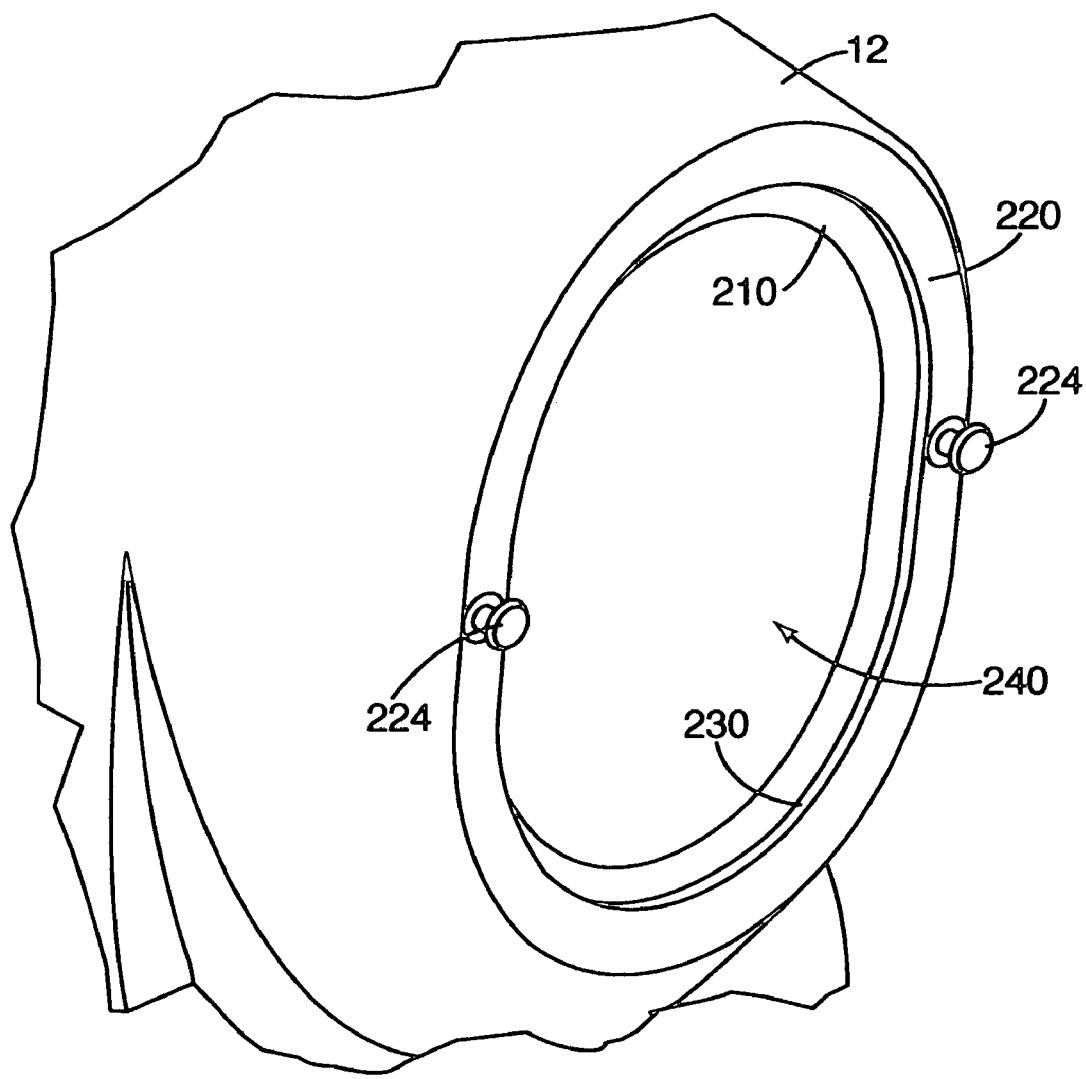
FIG. 17 is a perspective of a sealed window of the optical measurement instrument.

The shield 300 may be secured to the optical measuring instrument as depicted in FIG. 17 in any convention manner. Preferably, the shield includes clips 324 that releasably clips to pegs 224 of the optical measuring instrument. Of course, the shield may be secured to the optical measuring instrument by any conventional fitting as the application requires.

As with appreciated, the shield may be of paper or plastic or other material which may be disposable, cleanable, reusable or the like in order to address any contamination concerns that may exist in a particular application. The shield may also be disposable or reusable. In the case of reusable shields, the shield is preferably constructed of material that can withstand sterilization in a typical autoclave, hot steam, chemiclave or sterilizing system.

Line of Sight Viewing

Figure 15:
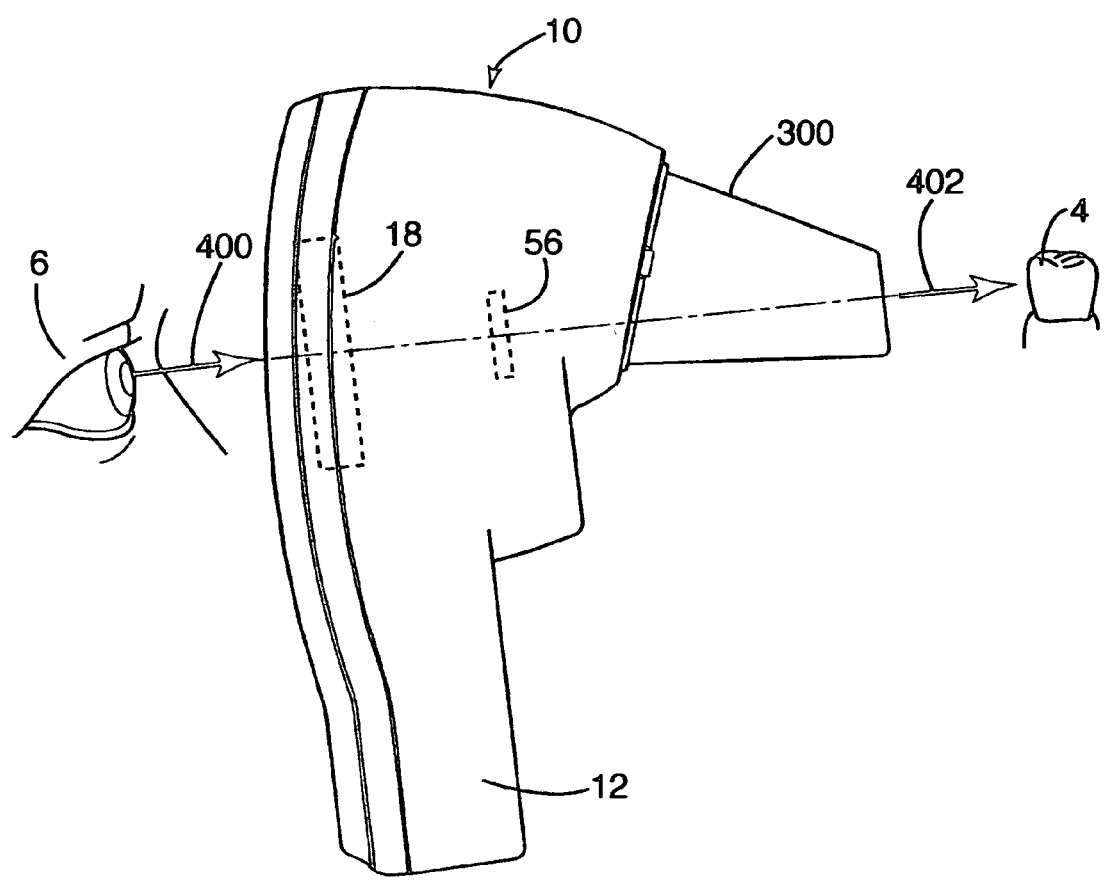
FIG. 15 is a side view of a line of sight feature of the optical measurement instrument.
Figure 16:
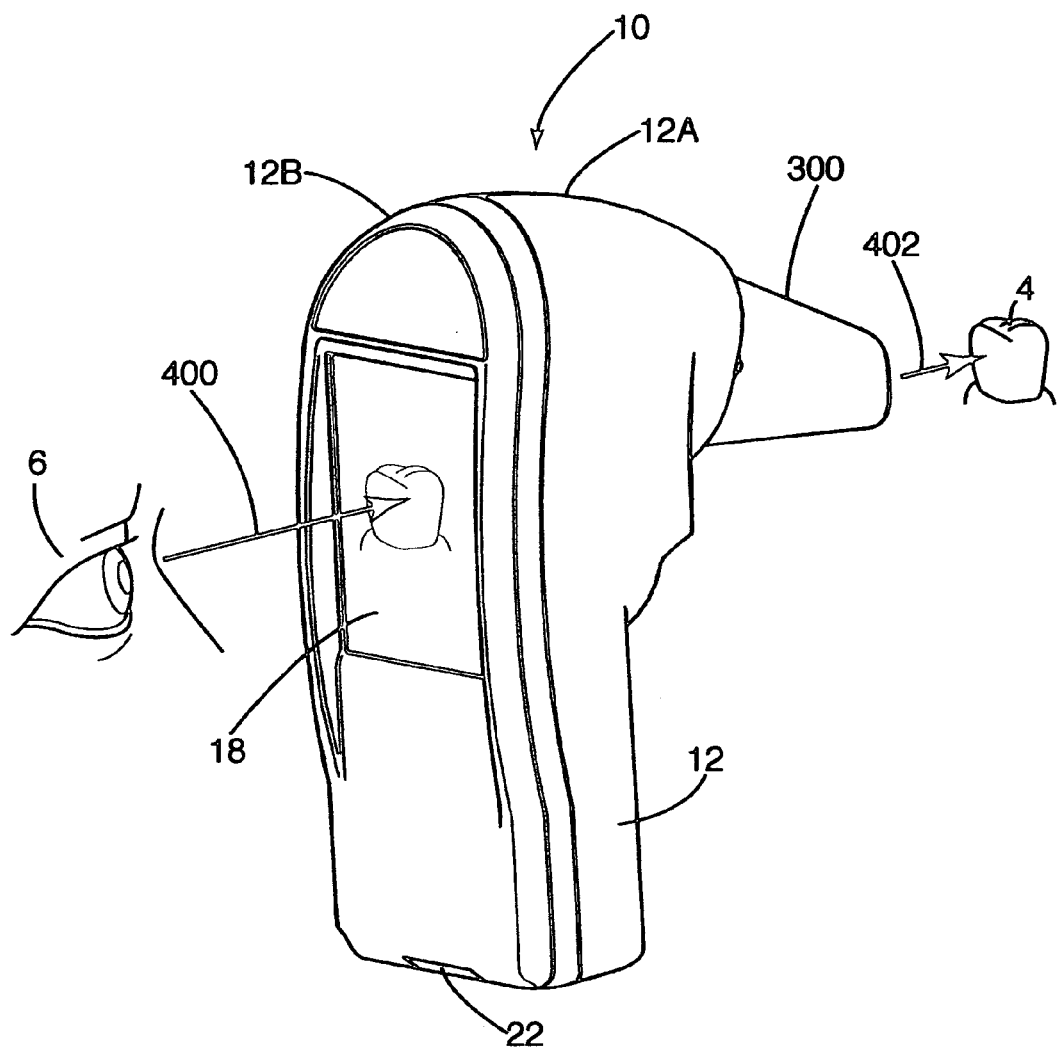
FIG. 16 is a perspective view of the line of sight feature.

FIGS. 15 and 16 illustrate the line of sight viewing of the preferred embodiment. The optical measuring instrument 10 includes housing 12 and display 18 mounted therein. As explained above, an image sensor is also included in the housing 12. The image sensor collects images from an image sensor view 402, also referred to as "line of sensing." The line of sensing projects outward from the housing 12, through the installed shield 300 toward the object for which an image is to be collected, for example the tooth 4. The object should be disposed in this line of sensing 402 so that the optical measurement instrument may sense and measure the optical characteristics of the object.

Once the image sensor takes a measurement of the object in the line of sensing 402, that measurement is processed by the processor of the instrument (see FIG. 6) and transferred to the LCD 18. The LCD displays the data as an image thereon in the preferred embodiment. The image may be magnified or reduced if desired. Of course, any conventional dynamic display may be used in place of a LCD.

With the image displayed on the display 18, an operator 6 may view the display along a line of viewing 400. This line of viewing 400 is aligned with the line of sensing 402 so that the operator 6 views the tooth on the display in the same perspective as the image sensor senses the tooth. Manipulation of the line of sensing 402 preferably corresponds to a different image being output on the display 18. For example, when an operator moves the device, and consequently the line of sensing 402, to the right of the tooth 4, the image output on the screen 18 will correspond to whatever object is to the right of the tooth. More basically, a user may manipulate the device to realign the line of sensing by viewing an image on the screen without having to reverse or otherwise alter his normal thought process for acquiring and viewing an image.

With reference to FIG. 15, the display 18 is preferably aligned in parallel behind the image sensor 56 in housing 12. And preferably, the display 18 is generally perpendicular to the line of sensing 402 and/or line of viewing 400. Of course, the screen 18, sensor 56, line of sensing and line of viewing may be aligned in other configurations so the line of viewing 400 is axially aligned with the line of sensing 402.

The optical measurement instrument 10 is configured in any way that allows the operator to manipulate the instrument 10 and simultaneously view the same image that the sensor senses on a display on the instrument without periodically having to look away from the display and realign the image sensor's line of sensing. Accordingly, the operator may view the display alone along line of viewing 400 to precisely align the line of sensing 402 so that the instrument collects the image of the tooth as desired.

Sealed Unit

With reference to FIGS. 16 and 17 the optical measurement instrument generally includes housing 12, divided into subparts 12a and 12b, display 18 and window 230. With particular reference to FIG. 17, the front portion of the housing 12 defines aperture 240 covered by window 230. The aperture allows illumination to be projected out from the interior of the housing 12 and allows light reflected from an object to enter back into the housing 12 and be sensed by an image sensor (not shown). The aperture 240 may be of a variety of configurations and sizes that facilitate illumination and sensing characteristics as desired.

The aperture is circumferentiated by an internal lip 210 that is preferably formed as part of the housing 12. Disposed over the lip is window or cover panel 230. Preferably, this cover is made from plastic, glass or other synthetic material that allows high efficiency transmission of light through it. Disposed between the lip 210 and the window 230 is seal 220. The seal may be any gasket or seal, for example a sealing adhesive, that prevents "pollutants"—meaning dust, dirt, debris, moisture, cleaning agents, and chemicals—from entering the interior of the housing body 12 through or around the aperture 240.

The display 18 is preferably sealed to or into the housing 12 in a manner that prevents pollutants from entering the interior as well. It is preferred that the display is touch sensitive and is able to provide a means to control and operate the device. In this manner, no difficult to clean around external buttons are included in the housing.

Subparts 12a and 12b are preferably seated together in a manner that also prevents pollutants from entering the interior of the housing body along the portions of the subparts where the subparts connect to or seat against one another.

As explained, all of the above elements, the sealed window 240, the mated subparts 12a, 12b, and the display 18, prevent pollutants from entering the interior of the device when the pollutants come in contact with the device, such as when the device is wiped down with cleaning or sterilizing agents, or when the device is dropped on a dirty floor. However, these elements do not significantly prevent the pollutants from entering the interior of the device if the device is fully submersed in pollutants, for example, if the device is submersed in liquid cleaning agents.

The device of the present invention in some embodiments may include a port 22 or other connection for communication with a docking station (FIG. 18), computing device and/or power source (not shown). Typically, it is difficult to seal this port to prevent pollutants from entering the interior of the housing 12.

The optical measurement instrument is easily sanitized and/or sterilized. Users may clean it by wiping it down without significant worry of leaking sanitizing or sterilizing agents or other cleaning agents into the interior of the housing 12, a consequence that potentially might damage the internal components of the instrument. Of course, care must be taken to prevent excessive exposure of a connection or port to pollutants to prevent those pollutants from entering the interior of the device. In periods of non-use, or use in dusty regions, the risk of dust or debris entering the housing is significantly decreased.

Dental Prosthesis Manufacture

The preferred process of creating a dental restoration or prosthesis from optical measurements taken from a damaged tooth or surrounding teeth will now be described. To begin, a dentist uses the preferred optical measuring instrument to measure the optical characteristics of a tooth or teeth that surround an area that was previously occupied by a tooth. These optical measurements are converted to an image or plurality of images in the optical measurement instrument. The images may be downloaded from the optical measurement instrument to a computer where they may be stored. Of course, the image may be stored in any appropriate electronic file format. Once the image is stored in the computer, it forms what is referred to as a restoration file. From this restoration file, the measured optical characteristics may be mathematically manipulated by the computer to be viewed as an average characteristic map, as a grid of individual characteristics, as a contoured characteristic map, or any other desirable format as will be appreciated by those skilled in the art.

Next, the dentist transmits the restoration file to a restorative prosthesis-manufacturing laboratory with any acceptable means. Preferably, however, the file is forwarded using electronic network correspondence.

At the lab, a technician downloads the restoration file to reconstruct the patient's mouth, and in particular, the new prosthetic replacement for the damaged or missing tooth. Software capable of this reconstruction is available from X-Rite, Incorporated of Grandville, Mich. After the technician creates the restorative prosthesis, an image of the prosthesis, preferably with the optical measuring instrument of the preferred embodiment.

The inlet of the prosthesis is inserted into an image of patient's mouth derived from the restoration file to determine quality and accuracy of the restoration. This may be done in several ways. First, the technician may use her own optical measuring instrument to take measurements of the prosthesis to create an image of the prosthesis also referred to as "prosthesis data." She then takes this image and inserts it into an image of the patient's mouth taken from the restoration file. Of course, the technician may also compare the prosthesis data to the image of the original tooth, if one exits. The technician conducts a comparison of the image of the tooth to the image of the patient's mouth and damaged tooth before the restoration is shipped from the lab. The technician may then determine the quality and accuracy of the restoration and decide whether or not to ship it to the dentist for installation in the patient's mouth.

In a second alternative embodiment, the technician may use the optical measuring instrument to take measurements of the prosthetic restoration to create an image of the prosthesis and send that image to the dentist. The dentist may then visually insert the new tooth image into an existing image of the patient's mouth to determine the quality and accuracy of the restoration. Based on his or her own judgment, the dentist may then contact the lab to confirm or decline the restoration. In cases where the restoration is confirmed, the lab will ship the restoration to the dentist for installation in the patient's mouth. In cases where the dentist declines the restoration because it is not an acceptable match, the lab constructs another restoration and takes a new image of that restoration. The new image is forwarded to the dentist to compare that new image to the image of the damaged tooth. This process may be repeated until an accurate restoration is created.

In a third alternative embodiment, the technician may simply create the prosthesis and send it to the dentist. The dentist uses her own optical measurement instrument to obtain an image of the prosthesis. That prosthesis data is visually inserted into an image of the patient's mouth or compared to an image of the damaged tooth to determine the quality and accuracy of the restoration. If the restoration is acceptable, the dentist will install it in the patient's mouth. If the restoration is unacceptable, the dentist may request the lab to create another restoration or alter the restoration in a manner to make it an accurate duplicate of the original tooth for which it was designed to replace.

Docking Station

Figure 18:
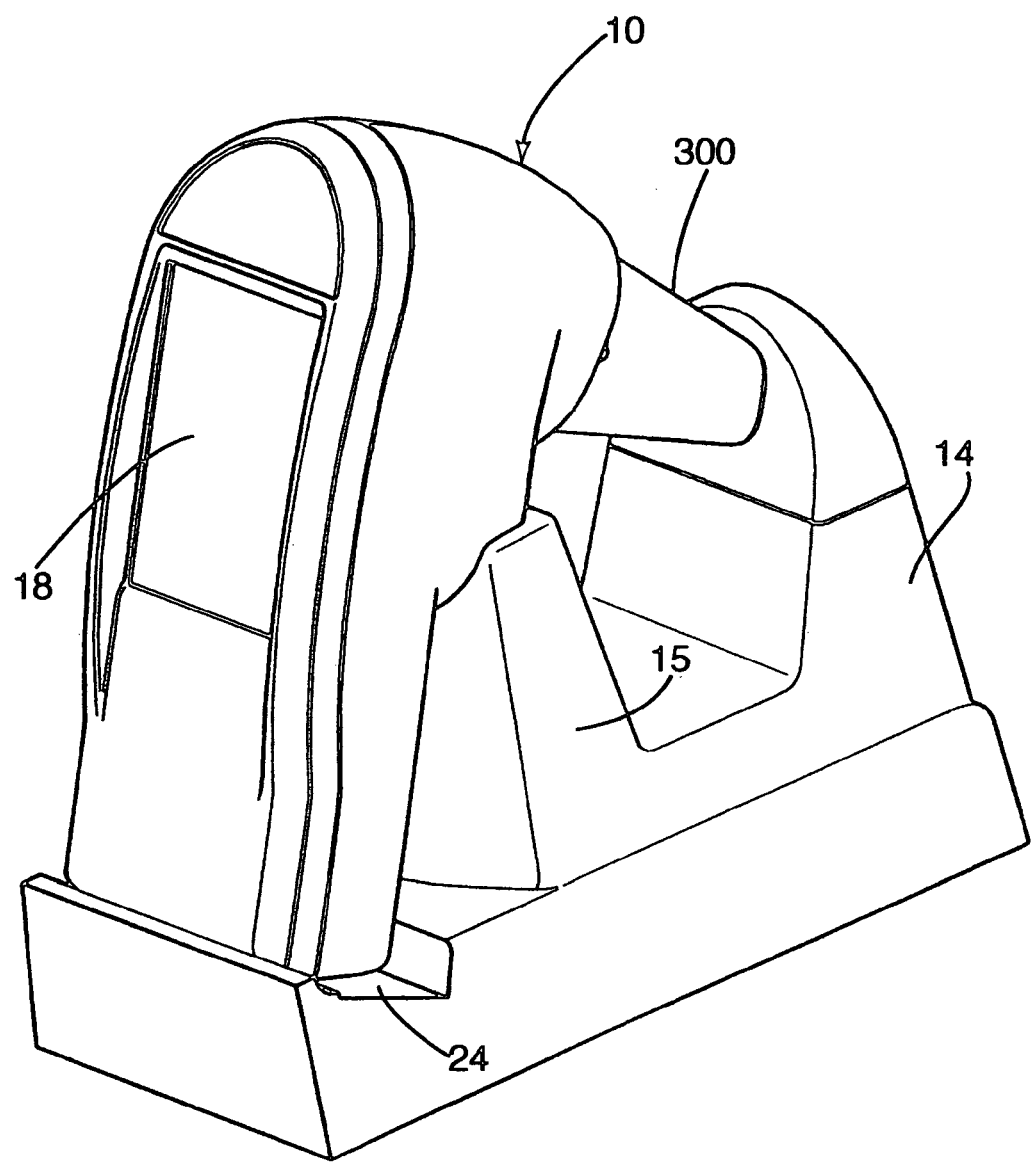
FIG. 18 is a perspective view of the optical measurement instrument in a docking station.

With reference to FIG. 18, the optical measurement instrument 10 docks or rests in docking station 14 when not in use or when downloading images from the instrument 10 to a computer (not shown) connected to the docking station for further analysis of these images or to forward those images to a third party. The docking station 14 includes support 15 to hold the instrument 10 in a ready-to-grasp position. The instrument also rests in port 24 that includes a plug (not shown) to interface with portal 22 (see FIG. 6) for download of images and recharging of power source 90 of the instrument 10. The docking station may also provide a data connection for download/upload of patient information and/or download/upload of image and modified patient information to/from the instrument 10. Of course any other information as desired may be downloaded/uploaded.

In an alternative embodiment, the instrument may include a transmitter and/or receiver so that it can communicate with another instrument, with a docking station and/or directly with a computing device using a wireless connection wherein data may be transported through radio frequencies, light modulations, or other remote wireless communication means.

The above descriptions are those of the preferred embodiments of the invention. Various alterations and changes can be made without departing from the spirit and broader aspects of the invention as defined in the appended claims, which are to be interpreted in accordance with the principles of patent law including the doctrine of equivalents. Any references to claim elements in the singular, for example, using the articles "a," "an," "the," or "said," is not to be construed as limiting the element to the singular.

The embodiments of the invention in which an exclusive property or privilege is claimed are defined as follows:

1. A shield for a device for measuring optical characteristics of an object in a field of view, the device having an illumination source comprising:
   a one-piece unitary hollow body including first and second ends, said first end including means for removably mounting said body on the measuring device, said second end defining an aperture through which the object is measured, said second end including a reference area integral with the body and proximate said aperture, said reference area being in the field of view.

2. A shield for a device for measuring optical characteristics of an object in a field of view, the device having an illumination source comprising:
   a body defining an aperture through which the object is measured;
   means for engaging said body against the measuring device whereby ambient light is restricted from entering said body;
   a reference area proximate said aperture, said reference area in the field of view; and
   means for indicating at least one of the origin of the shield, lot number of the shield, expiration date of the shield and patient information, said indicating means disposed proximate said aperture and in said field of view.

3. The shield of claim 2 including a peripheral wall that restricts ambient light from entering said body through said aperture.

4. The shield of claim 3 wherein said peripheral wall circumferentiates said aperture.

5. The shield of claim 2 wherein said body is disposable.

6. The shield of claim 2 wherein said body is reusable.

7. A shield for a color measuring device used in dental applications comprising:
   a body defining a cavity and including first and second ends, said first end separated from said second end a pre-selected distance;
   a first aperture defined by said first end to be disposed in a position chosen from against and adjacent an object to be color measured;
   a second aperture defined by said second end to be disposed proximate the color measurement device; and
   a reference area associated with said body proximate said first aperture.

8. The shield of claim 7 wherein the shield is at least one of disposable and resealable to prevent contamination from passing from a first patient to subsequent patients.

9. The shield of claim 8 comprising means for releasably attaching said body to the color-measuring device.

10. A shield for a device used to measure the color of dental objects within a field of view comprising a one-piece integral body defining a cavity through which illumination passes, said body being of a predetermined length, said body including means for attaching said body to an instrument, said body including an integral illumination reference area in the field of view.

11. The shield of claim 10 wherein said attaching means comprises means for releasably securing said body to the color measuring device.

12. The shield of claim 11 wherein said body is disposable.

13. The shield of claim 12 wherein said body is opaque to prevent ambient light from entering said cavity.

14. The shield of claim 13 comprising indicia means for providing information captured in the field of view.

15. An instrument for acquiring a color image of a tooth within a field of view, said instrument comprising:
   a housing;
   an illumination source within said housing for illuminating the field of view;
   an image sensing device within said housing for sensing an image of the tooth; and
   a disposable shield including a first end removably connected to said housing and a second end defining an aperture within the field of view, the shield providing a desired spacing between the tooth and the image sensing device when the second end is placed against a portion of a patient's mouth, said second end including a reference area.

16. The instrument of claim 15 wherein said first end provides a light tight seal against said housing.

17. The shield of claim 1 wherein said reference area is adjacent the aperture and wherein the reference area is a uniform color.

18. The shield of claim 17 wherein the reference area includes portions on opposite sides of the aperture.

* * * * *